US010155176B1

(12) United States Patent
Feuer et al.

(10) Patent No.: US 10,155,176 B1
(45) Date of Patent: Dec. 18, 2018

(54) PROCESS FOR THE PRODUCTION OF A CONCENTRATED CANNABINOID PRODUCT

(71) Applicant: Healer, LLC, Falmouth, ME (US)

(72) Inventors: Bradley Feuer, Falmouth, ME (US); Dustin Sulak, Durham, ME (US); William J. Christ, Andover, MA (US); Ross J. Lapenta, Sandy River Plantation, ME (US); Michael Feuer, St. Louis, MO (US)

(73) Assignee: Healer, LLC, Falmouth, ME (US)

(*) Notice: Subject to any disclaimer, the term of this patent is extended or adjusted under 35 U.S.C. 154(b) by 0 days.

(21) Appl. No.: 15/803,010

(22) Filed: Nov. 3, 2017

Related U.S. Application Data

(60) Provisional application No. 62/417,021, filed on Nov. 3, 2016.

(51) Int. Cl.
| | |
|---|---|
| *B01D 11/04* | (2006.01) |
| *C07C 37/82* | (2006.01) |
| *B01D 61/14* | (2006.01) |
| *B01D 61/02* | (2006.01) |
| *B01D 61/58* | (2006.01) |
| *B01D 69/02* | (2006.01) |
| *B01D 71/02* | (2006.01) |
| *B01D 15/08* | (2006.01) |
| *C07D 311/80* | (2006.01) |

(52) U.S. Cl.
CPC ...... *B01D 11/0415* (2013.01); *B01D 11/0492* (2013.01); *B01D 15/08* (2013.01); *B01D 61/027* (2013.01); *B01D 61/145* (2013.01); *B01D 61/58* (2013.01); *B01D 69/02* (2013.01); *B01D 71/02* (2013.01); *C07C 37/82* (2013.01); *C07D 311/80* (2013.01); *B01D 2311/02* (2013.01); *B01D 2311/06* (2013.01); *B01D 2311/2626* (2013.01); *B01D 2315/10* (2013.01); *B01D 2325/20* (2013.01)

(58) Field of Classification Search
CPC ............. B01D 11/0415; B01D 69/02; B01D 11/0492; B01D 61/145; B01D 15/08; B01D 71/02; B01D 61/58; B01D 61/027; B01D 2325/20; B01D 2311/02; B01D 2311/2626; B01D 2315/10; B01D 2311/06; C07C 37/82; C07D 311/80
See application file for complete search history.

(56) References Cited

U.S. PATENT DOCUMENTS

| | | |
|---|---|---|
| 4,716,120 A | 12/1987 | Tsay et al. |
| 5,301,694 A | 4/1994 | Raymond et al. |
| 5,384,395 A | 1/1995 | Berrens |
| 6,033,895 A | 3/2000 | Garger et al. |
| 6,171,638 B1 | 1/2001 | Gugger et al. |
| 7,771,494 B2 | 8/2010 | Rangachari et al. |
| 8,344,178 B2 | 1/2013 | Rangachari et al. |
| 8,426,333 B2 | 4/2013 | Bishop et al. |
| 8,431,508 B2 | 4/2013 | Bishop et al. |
| 8,431,509 B2 | 4/2013 | Bishop et al. |
| 8,980,941 B2 | 3/2015 | Hospodor |
| 9,937,218 B2 * | 4/2018 | Towle ................ A61K 36/185 |
| 2003/0017216 A1 | 1/2003 | Schmidt et al. |
| 2005/0037474 A9 | 2/2005 | Sheabar et al. |
| 2005/0266108 A1 | 12/2005 | Flockhart et al. |
| 2008/0179246 A1 | 7/2008 | De Magalhaes Nunes Da Ponte et al. |
| 2009/0131244 A1 | 5/2009 | Bishop et al. |
| 2013/0079531 A1 | 3/2013 | Barringer |
| 2015/0038567 A1 | 2/2015 | Herkenroth et al. |

FOREIGN PATENT DOCUMENTS

| | | |
|---|---|---|
| CN | 102292452 B | 1/2015 |
| EP | 1385595 B1 | 5/2012 |
| EP | 1536810 B1 | 8/2012 |
| JP | 5913500 B2 | 4/2016 |

OTHER PUBLICATIONS

Barakat, M.A., "New Trends in Removing Heavy Metals from Industrial Wastewater," 2011, Arabian J. Chem, 4:361-377, 17 pages.
Bucar, F., et al., Natural Product Isolation—How to Get From Biological Material to Pure Compounds, 2013, Nat Prod Rep 20:525-545, 21 pages.
Cassano, A., et al., "A Two-Step Nanofiltration Process for the Production of Phenolic-Rich Fractions from Artichoke Aqueous Extracts," 2015, Int J Mol Sci, 16:8968-8987, 20 pages.
Galal, A.M., et al., "Naturally Occurring and Related Synthetic Cannabinoids and their Potential Therapeutic Applications," 2009, Recent Patents on CNS Drug Discovery, 4:112-136, 25 pages.
Peev, G., et al., "Solvent Extraction of Rosmrinic Acid from Lemon Balm and Concentration of Extract by Nanofiltration: Effect of Plant Pre-Treatment by Supercritical Carbon Dioxide," 2011, Chemical Engineering Research and Design, 89:2236-2243, 8 pages.
Romano, L.L., et al., "Cannabis Oil: Chemical Evaluation of an Upcoming Cannabis-Based Medicine," 2013, Cannabinoids, 1/1:1-11, 11 pages.
Russo, E.B., "Taming THC: Potential Cannabis Synergy and Phytocannabinoid-Terpenoid Entourage Effects," 2011, British J of Pharma, 163:1344-1364, 21 pages.

* cited by examiner

*Primary Examiner* — John M Mauro
(74) *Attorney, Agent, or Firm* — Stinson Leonard Street LLP

(57) ABSTRACT

The invention relates to methods for preparing a concentrated cannabinoid product optionally also containing an array of terpenes, flavonoids, and other phytoconstituents from a cannabinoid-containing extract feed. The cannabinoid-containing extract feed is contacted with an adsorbent to produce a pre-treated extract which is then subjected to one or more filtration steps, and recovering the concentrated cannabinoid product utilizing an extractant or an evaporator.

23 Claims, 26 Drawing Sheets

PROCESS FOR THE PRODUCTION OF A CONCENTRATED CANNABINOID PRODUCT

REFERENCE TO RELATED APPLICATIONS

This application claims benefit of U.S. Provisional Application No. 62/417,021, filed Nov. 3, 2016, the entire disclosure of which is incorporated herein by reference.

FIELD OF THE INVENTION

The invention relates to a process for preparing a concentrated cannabinoid product containing an array of cannabinoids, and optionally terpenes, flavonoids, and other phytoconstituents. The concentrated cannabinoid product can be used in medicinal *cannabis* treatment therapies.

BACKGROUND OF THE INVENTION

*Cannabis* is a plant material containing many useful compounds and components such as cannabinoids, terpenes, and flavonoids. *Cannabis* and extracts prepared from *cannabis* containing these various components have utility in medicinal *cannabis* treatment therapies.

Particularly notable are the cannabinoids tetrahydrocannabinolic acid (THCA), $\Delta^8$ tetrahydrocannabinolic acid ($\Delta^8$ THCA), $\Delta^9$ tetrahydrocannabinolic acid ($\Delta^9$ THCA), tetrahydrocannabinol (THC), $\Delta^8$ tetrahydrocannabinol ($\Delta^8$ THC), $\Delta^9$ tetrahydrocannabinol ($\Delta^9$ THC), cannabidiolic acid (CBDA), cannabidiol (CBD), cannabinol (CBN), cannabigerolic acid (CBGA), cannabigerol (CBG), cannabigerolic acid (CBCA), cannabichromene (CBC), and tetrahydrocannabivarin (THCV).

In addition to these major cannabinoids, terpenes typically found in *cannabis* include: trans-nerolidol, terpinolene, terpineol, saniene hydrate, L-fenchone, guaiol, geraniol, y-terpinene, b-pinene, a-terpinene, a-humulene, a-cedrene, a-Pinene, R-Limonene, S-Camphor, fenchyl alcohol, R-camphor, −/+borneol, +pulegone, valencene, trans-caryophyllene, p-mentha 1,5-diene, ocimene, nerol, linalool, isoborneol, hexahydrothymol, geranyl acetate, farnesene, eucalyptol, cis-nerolidol, camphor, camphene, b-myrcene, carene, -isopulegol, caryophyllene oxide, a-bisabolol, +fenchone, and +cedrol.

Flavonoids typically found in *cannabis* include quercetin, luteolin, kaempferol, cannaflavin A, and apigenin.

Other components present in *cannabis* plant material may include flavins, chlorophyll A, and chlorophyll B.

Isolation, concentration, or purification of the cannabinoids, terpenes, flavonoids, and/or other phytoconstituents present in *cannabis* may be necessary in order to observe or amplify the medicinal benefit of the respective component.

Current practices regarding preparation of cannabinoid products containing these components typically include subjecting the raw plant material to an extracting solvent such as ethanol to produce a bulk extract. The solvent is then removed via open evaporation, reduced pressure, or by flowing a gas stream over the surface of the bulk extract, sometimes at an elevated temperature. Issues arising from these practices include poor scalability, long processing times, destruction/evaporation of the more volatile desirable components, and difficulty in isolating or concentrating specific components.

There remains a need for a process for producing a concentrated cannabinoid product from *cannabis* extracts of varying purity or raw *cannabis* plant material. The present invention provides a process for producing a concentrated cannabinoid product using a unique adsorption and filtration system whereby a highly concentrated cannabinoid product is obtained while maintaining an amount of more volatile components present in the raw plant material, such as volatile terpenes.

SUMMARY OF THE INVENTION

Briefly, therefore, the present invention is directed to a process for preparing a concentrated cannabinoid product optionally further containing an array of terpenes, flavonoids, and other phytoconstituents.

In one embodiment, the process comprises contacting a cannabinoid-containing extract feed comprising cannabinoids and a solvent with an adsorbent to adsorb large molecule impurities from the cannabinoid-containing extract feed and produce a pre-treated extract. The pre-treated extract is then contacted with a first filter having a 400-5,000 dalton MWCO (molecular weight cut-off) to produce a first retentate comprising large molecular weight impurities and a first permeate comprising cannabinoids, wherein the concentration of cannabinoids in the first permeate is higher than the concentration of cannabinoids in the first retentate. The first permeate and an extractant are combined to form a filtrate extraction mixture comprising an extract phase comprising cannabinoids and a raffinate phase comprising solvent from the cannabinoid-contacting extract feed. The concentrated cannabinoid product is recovered from the extract phase.

In another embodiment, the process comprises contacting a cannabinoid-containing extract feed comprising cannabinoids and a solvent with an adsorbent to adsorb large molecule impurities from the cannabinoid-containing extract and produce a pre-treated extract. The pre-treated extract is contacted with a first filter having a 400-5,000 dalton MWCO to produce a first retentate comprising large molecular weight impurities and a first permeate comprising cannabinoids, wherein the concentration of cannabinoids in the first permeate is higher than the concentration of cannabinoids in the first retentate. The first permeate is then contacted with a second filter having a 150-1,000 dalton MWCO to produce a second retentate comprising cannabinoids and a second permeate comprising small molecular weight impurities, wherein the concentration of cannabinoids in the second retentate is higher than the concentration of cannabinoids in the second permeate. The second retentate and an extractant are combined to form a filtrate extraction mixture comprising an extract phase comprising cannabinoids and a raffinate phase comprising solvent from the cannabinoid-containing extract feed. The concentrated cannabinoid product is recovered from the extract phase.

In a still further embodiment, the process comprises contacting a cannabinoid-containing extract feed comprising cannabinoids and a solvent with an adsorbent to adsorb large molecule impurities from the cannabinoid-containing extract feed and produce a pre-treated extract. The pre-treated extract is contacted with a first filter having a 400-5,000 dalton MWCO to produce a first retentate comprising large molecular weight impurities and a first permeate comprising cannabinoids, wherein the concentration of cannabinoids in the first permeate is higher than the concentration of cannabinoids in the first retentate. Water is added to the first permeate to form a water-adjusted first permeate having a water content of from about 20 wt % to about 40 wt %. The water-adjusted first permeate is contacted with the first filter to produce a second permeate comprising small molecular weight impurities and a second retentate comprising cannabinoids, wherein the concentration of cannabinoids in the second retentate is higher than the concentration of cannabinoids in the second permeate. The second retentate and an extractant are combined to form a filtrate extraction mixture comprising an extract phase comprising cannabinoids and a raffinate phase comprising solvent from the cannabinoid-containing extract feed. The concentrated cannabinoid product is recovered from the extract phase.

In another embodiment, the process comprises contacting a cannabinoid-containing extract feed comprising cannabinoids and a solvent with an adsorbent to adsorb large molecule impurities from the cannabinoid-containing extract feed and produce a pre-treated extract. The pre-treated extract is then contacted with a first filter to produce a first retentate comprising large molecular weight impurities and a first permeate comprising cannabinoids, wherein the concentration of cannabinoids in the first permeate is higher than the concentration of cannabinoids in the first retentate. The first permeate and an extractant are combined to form a filtrate extraction mixture comprising an extract phase comprising cannabinoids and a raffinate phase comprising solvent from the cannabinoid-contacting extract feed. The concentrated cannabinoid product is recovered from the extract phase. At least about 75% by weight of compounds having a molecular weight greater than about 500 daltons contained in the pre-treated extract are retained in the first retentate.

In another embodiment, the process comprises contacting a cannabinoid-containing extract feed comprising cannabinoids and a solvent with an adsorbent to adsorb large molecule impurities from the cannabinoid-containing extract and produce a pre-treated extract. The pre-treated extract is contacted with a first filter to produce a first retentate comprising large molecular weight impurities and a first permeate comprising cannabinoids, wherein the concentration of cannabinoids in the first permeate is higher than the concentration of cannabinoids in the first retentate. The first permeate is then contacted with a second filter to produce a second retentate comprising cannabinoids and a second permeate comprising small molecular weight impurities, wherein the concentration of cannabinoids in second retentate is higher than the concentration of cannabinoids in the second permeate. The second retentate and an extractant are combined to form a filtrate extraction mixture comprising an extract phase comprising cannabinoids and a raffinate phase comprising solvent from the cannabinoid-containing extract feed. The concentrated cannabinoid product is recovered from the extract phase. At least about 75% by weight of compounds having a molecular weight greater than about 500 daltons contained in the pre-treated extract are retained in the first retentate and at least about 75% by weight of compounds having a molecular weight less than about 200 daltons contained in the first permeate are transferred to the second permeate.

In still a further embodiment, the process comprises contacting a cannabinoid-containing extract feed comprising cannabinoids and a solvent with an adsorbent to adsorb large molecule impurities from the cannabinoid-containing extract feed and produce a pre-treated extract. The pre-treated extract is contacted with a first filter to produce a first retentate comprising large molecular weight impurities and a first permeate comprising cannabinoids, wherein the concentration of cannabinoids in the first permeate is higher than the concentration of cannabinoids in the first retentate. Water is added to the first permeate to form a water-adjusted first permeate having a water content of from about 20 wt % to about 40 wt %. The water-adjusted first permeate is contacted with the first filter to produce a second permeate comprising small molecular weight impurities and a second retentate comprising cannabinoids, wherein the concentration of cannabinoids in the second retentate is higher than the concentration of cannabinoids in the second permeate. The second retentate and an extractant are combined to form a filtrate extraction mixture comprising an extract phase comprising cannabinoids and a raffinate phase comprising solvent from the cannabinoid-containing extract feed. The concentrated cannabinoid product is recovered from the extract phase. At least about 75% by weight of compounds having a molecular weight greater than about 500 daltons contained in the pre-treated extract are retained in the first retentate and at least about 75% by weight of compounds having a molecular weight less than about 200 daltons contained in the water-adjusted first permeate are transferred to the second permeate.

Other objects and features will be in part apparent and in part pointed out hereinafter.

DETAILED DESCRIPTION OF THE PREFERRED EMBODIMENTS

Figure 1:
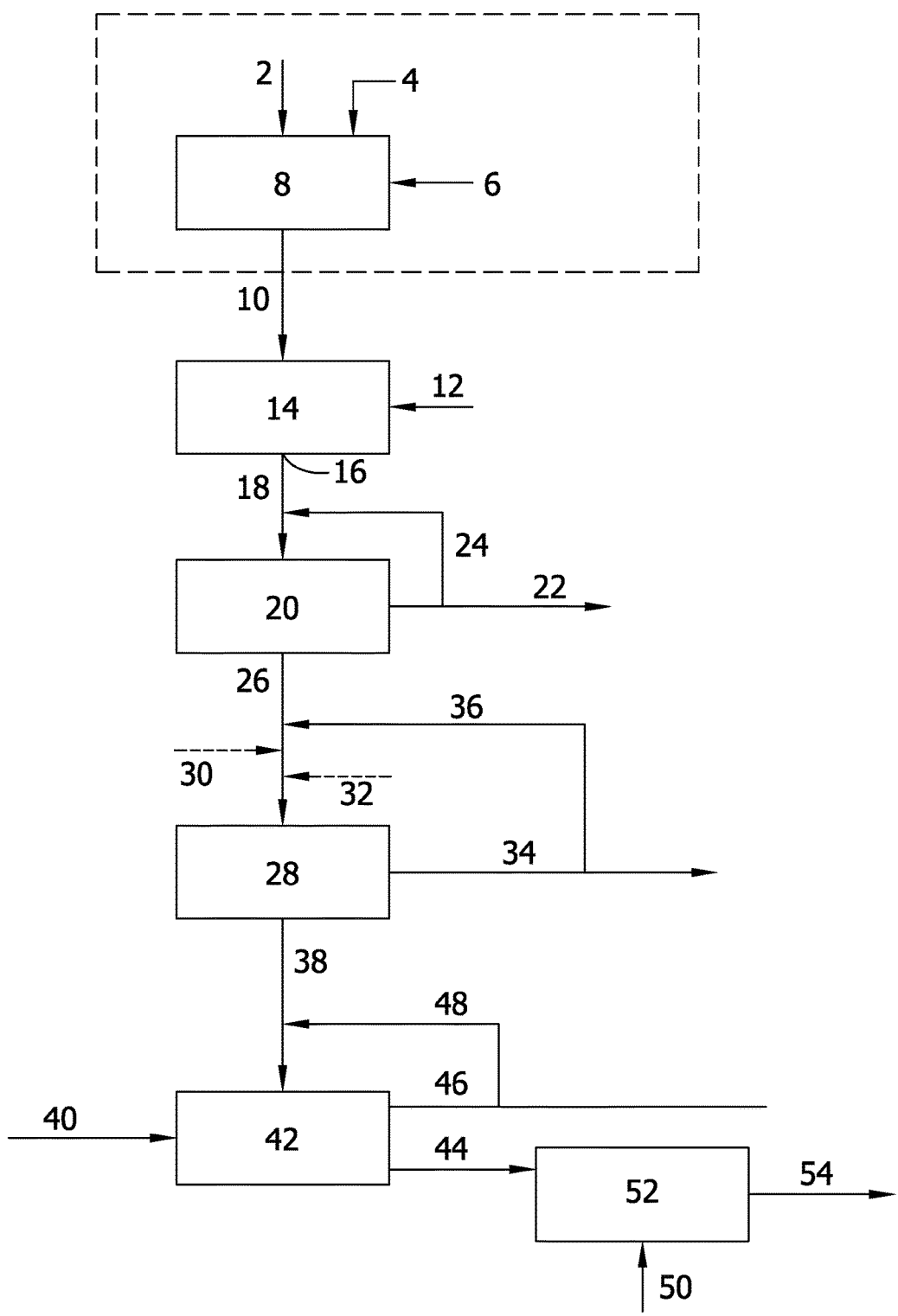
FIG. 1 shows the process flow schematic of a process for the production of a concentrated cannabinoid product wherein a first filter and a second filter are used.

In one embodiment, the process of the present invention includes contacting a cannabinoid-containing extract feed with an adsorbent to adsorb large molecule impurities (e.g., non-cannabinoid impurities such as chlorophyll) from the cannabinoid-containing extract feed and produce a pre-treated extract. The pre-treated extract is then contacted with a first filter to produce a first retentate, comprising large molecular weight impurities, and a first permeate, comprising cannabinoids. In addition to cannabinoids, the first permeate may also comprise terpenes, flavonoids, other phytoconstituents, and combinations thereof. The first permeate is combined with an extractant to form a filtrate extraction mixture comprising an extract phase comprising cannabinoids and a raffinate phase comprising solvent(s) from the cannabinoid-containing extract feed.

In a further embodiment, a second filter is utilized. The first permeate is contacted with a second filter to produce a second retentate comprising cannabinoids and a second permeate comprising small molecular weight impurities. In addition to cannabinoids, the second retentate may also comprise terpenes, flavonoids, other phytoconstituents, and combinations thereof. The second retentate is then combined with an extractant to form a filtrate extraction mixture comprising an extract phase comprising cannabinoids and a raffinate phase comprising solvent(s) from the cannabinoid-containing extract feed.

In another embodiment, a cannabinoid-containing extract feed is contacted with an adsorbent to adsorb large molecule impurities from the cannabinoid-containing extract feed and produce a pre-treated extract. The pre-treated extract is then contacted with a first filter having a molecular weight cut-off (MWCO) of from about 400 to about 5,000 daltons to produce a first retentate comprising large molecular weight impurities, and a first permeate comprising cannabinoids. The first permeate is then contacted with a second filter having a MWCO of from about 150 to about 1,000 daltons to produce a second retentate comprising cannabinoids and a second permeate comprising small molecular weight impurities. In addition to cannabinoids, the second retentate may also comprise terpenes flavonoids, other phytoconstituents, and combinations thereof. The second retentate is combined with an extractant to form a filtrate extraction mixture comprising an extract phase comprising cannabinoids and a raffinate phase comprising solvent(s) from the cannabinoid-containing extract feed.

In these and other embodiments, a concentrated cannabinoid product is recovered from the extract phase, as described in further detail below.

Preparing a Cannabinoid-Containing Extract Feed:

Starting material for preparing a cannabinoid-containing extract feed may be any suitable *cannabis* starting material as known in the art. Non-limiting examples include raw *cannabis* plant material, *cannabis* extracts produced by exposing *cannabis* plant material to a solvent, commercially available cannabinoid-containing *cannabis* extracts, tinctures, oils, liquid concentrates, or any mixture containing at least some concentration of cannabinoids. The term "raw *cannabis* plant material," "raw *cannabis*," "raw *cannabis* material," and "plant material" should be understood to encompass the use of any portion of a *cannabis* plant. This includes, but is not limited to, flowers, stems, nodes, leaves, pistils, colas, calyxs, trichomes, seed, stalk, buds (including dormant buds, axillary buds, and terminal buds), petiole, rachis, bract, and roots. The term "*cannabis*" should be understood to encompass all plants of the genus *cannabis* and/or the family cannabaceae. This will also be understood to encompass, without limitation, all plants of the species *cannabis sativa, cannabis* indica, and *cannabis ruderalis*.

*Cannabis* plant materials known to be exposed to heavy doses of pesticides, such as herbicides or insecticides, are typically less preferred as starting materials for preparing the cannabinoid-containing extract feed. Additionally, any *cannabis* material that would not be viewed as suitable for ingestion (e.g. moldy, decomposed, etc.) is typically less preferred as a starting material.

Raw *cannabis* plant material (including leaves, stems, flowers, stalks, etc.) used as the starting material for preparing the cannabinoid-containing extract feed may be subjected to conventional extraction processes known in the art, including extraction with solvents such as dichloromethane, chloroform, hexane, tetrahydrofuran, isopropyl alcohol, methanol, carbon dioxide, butane, ethyl acetate, 2-methyltetrahydrofuran, ethanol, and ionic liquids. For example, in one embodiment the solvent used to prepare the cannabinoid-containing extract feed comprises ethanol. Several extraction techniques known in the field are described in Franz Bucar et al., *Natural Product Isolation—How to Get from Biological Material to Pure Compounds*, Nat. Prod. Rep., 2013, 30, 525-545, the contents of which are incorporated herein by reference. While lipophilic and organic solvents may be used for preparing a cannabinoid-containing extract feed from raw *cannabis* plant material, some of these may be toxic at low concentrations and introduce potential carcinogenic contamination. Therefore, certain lipophilic and organic solvents may be less preferred. Typically, the solvent used to prepare a cannabinoid-containing extract feed is neutral, mildly acidic, or mildly basic. In one embodiment, the pH of the solvent may be from about 6.5 to about 7.5, from about 6.6 to about 7.4, or from about 6.7 to about 7.3.

In preparing a cannabinoid-containing extract feed, *cannabis* plant material (either fresh or dried) is added to an extraction vessel. If fresh *cannabis* is used, the plant material may be frozen directly in the extraction vessel to aid in breaking up the material. For example, the plant material may be frozen with liquid nitrogen. Thereafter, a solvent (e.g., ethanol) along with a suitable grinding media is typically added to the extraction vessel and the contents of the extraction vessel are then agitated (e.g., mechanically agitated with an impeller) until the *cannabis* plant material is substantially reduced to a greenish mixture containing a suspension of fine particulate plant material. Typically, the contents of the extraction vessel may be agitated for a period of from about 2 to about 4 hours, although longer or shorter periods may be employed. The resulting mixture from the extraction vessel may then be used as the cannabinoid-containing extract feed for the process of the present invention.

In one embodiment, the weight of the grinding media added to the extraction vessel is approximately the same as the weight of the starting plant material added to the extraction vessel. Suitable grinding media may comprise zirconia grinding balls. In a specific embodiment, the zirconia grinding balls are about 2 mm in diameter. Other suitable grinding media may include any particle size reduction media useful for preparing a cannabinoid-containing extract feed. Suitable methods for preparing a cannabinoid-containing extract feed include high sheer stirring, temperature controlled media milling, high energy media milling, and temperature controlled high energy media milling.

When ethanol (e.g., anhydrous 200 proof USP grade ethanol) is used as the extraction solvent, the cannabinoid-containing extract feed is typically prepared using less than about 25 ml or less than about 15 ml of ethanol per gram of raw *cannabis* material added to the extraction vessel. The ethanol added to the extraction vessel may be chilled (i.e. below room temperature). For example, the ethanol used as the extraction solvent may be chilled to a temperature of below about 20° C., below about 15° C., below about 10° C., below about 5° C., below about 0° C., below about −5° C., below about −10° C., below about −15° C., below about −20° C., or below about −25° C. The temperature of the ethanol used as the extraction solvent may be from about −30° C. to about 20° C., from about −25° C. to about 15° C., from about −25° C. to about 10° C., from about −25° C. to about 5° C., from about −20° C. to about 0° C., or from about −15° C. to about −5° C. As discussed in further detail below, after the cannabinoid-containing extract feed is prepared, the temperature of the extract feed may be raised in order to provide optimal conditions for the downstream processing equipment that is used.

Although dried or fresh *cannabis* may be used as a starting material to prepare the cannabinoid-containing extract feed, enhanced results have been observed where the cannabinoid-containing extract feed has a water content less than about 30 wt %. In one embodiment, the cannabinoid-containing extract feed has a water content of less than about 25 wt %, less than about 20 wt %, less than about 15 wt %, less than about 10 wt %, or less than about 5 wt %. Accordingly, in some embodiments, the *cannabis* plant material and solvent(s) used to prepare the cannabinoid-containing extract feed are selected based upon their low water content.

Although preparation of a cannabinoid-containing extract feed utilizing ethanol as the extraction solvent and certain process conditions has been particularly described, the process for preparing a concentrated cannabinoid product is not limited to extract feeds prepared in this fashion. Further, as noted above, commercially available cannabinoid-containing *cannabis* extracts, tinctures, oils, liquid concentrates, or any mixture containing at least some concentration of cannabinoids may be suitably used as the cannabinoid-containing extract feed for the process of the present invention.

One skilled in the art will appreciate that the composition of the final concentrated cannabinoid product (on a weight basis, volume basis, etc.), including the concentration of cannabinoids contained therein, will be dependent to an extent upon the composition of the cannabinoid-containing extract feed.

Producing a Pre-Treated Extract:

A pre-treated extract is prepared by contacting the cannabinoid-containing extract feed comprising cannabinoids with an adsorbent to adsorb large molecule impurities and other contaminants from the extract feed. Typically, the cannabinoid-containing extract feed and a particulate adsorbent are placed in a pre-treatment vessel and mixed. After mixing, the contents of the pre-treatment vessel are passed through a pre-treatment filter to remove the particulate adsorbent and obtain the pre-treated extract.

Pre-treatment by contact with an adsorbent removes at least a portion of impurities and undesirable components from the cannabinoid-containing extract feed, including components that may make the final concentrated cannabinoid product less appealing to consumers. Non-limiting examples of the impurities believed to be removed by pre-treatment, include fertilizers, insecticide dust, pesticides, herbicides, chlorophyll, cellulose fragments, high molecular weight waxes, high molecular weight biological fragments, and mixtures thereof. It is particularly notable that the removal of some or all of the chlorophyll present in the cannabinoid-containing extract feed tends to improve the taste and produce a lighter colored final product. Pre-treatment is also believed to remove at least a portion of metals (e.g., arsenic, cadmium, mercury, ferric and ferrous iron, lead, cobalt, nickel, and chromium) present in the cannabinoid-containing extract feed.

In one embodiment, at least about 70%, at least about 75%, at least about 80%, at least about 85%, at least about 90%, at least about 95%, at least about 97%, or at least about 99% on a weight basis of the impurities and undesirable components are removed from the cannabinoid-containing extract feed by pre-treatment with an adsorbent.

Non-limiting examples of suitable adsorbents include charcoal, activated charcoal, silica (diatomaceous earth), magnesium silicate, and mixtures thereof. Activated charcoal may be selected from the group consisting of coconut derived charcoal, wood derived charcoal, and combinations thereof. Activated charcoal produced from animal matter (e.g., bone source material) is generally less preferred than activated charcoal produced from plant matter.

Suitable activated charcoal includes the product sold under the tradename DARCO, commercially available from Cabot Corporation (Boston, Mass.) or decolorizing activated charcoal commercially available from Sigma-Aldrich Co. (St. Louis, Mo.), for example, 100 mesh DARCO G-60 and 100 mesh decolorizing activated charcoal. Activated charcoal adsorbents are typically selected such that the activated charcoal has a minimum methylene blue absorption of 15 g/100 g.

Suitable magnesium silicate includes the product sold under the tradename FLORISIL, commercially available from Sigma-Aldrich Co. (St. Louis, Mo.).

Suitable silica includes the diatomaceous earth product sold under the tradename CELITE 545, commercially available from Sigma-Aldrich Co. (St. Louis, Mo.) and SiliCycle UltraPure, commercially available from SiliCycle Inc. (Quebec City, Canada).

In one embodiment the adsorbent comprises a mixture of activated charcoal, magnesium silicate, and/or silica.

Generally, charcoal, activated charcoal, and magnesium silicate adsorbents have an average particle size of less than about 300 μm, less than about 275 μm, less than about 250 μm, less than about 200 μm, less than about 175 μm or less than about 150 μm. For example, from about 50 μm to about 300 μm, from about 75 μm to about 250 μm, from about 100 μm to about 200 μm, or from about 125 μm to about 175 μm.

Generally, silica and diatomaceous earth adsorbents have an average particle size of less than about 500 μm, less than about 450 μm, less than about 400 μm, less than about 350 μm, less than about 300 μm, less than about 200 μm, less than about 100 μm, less than about 50 μm, less than about 25 μm, or less than about 10 μm. For example, silica and diatomaceous earth adsorbents may have an average particle size of from about 10 μm to about 500 from about 15 μm to about 400 from about 20 μm to about 300 from about 20 μm to about 200 from about 25 μm to about 150 or from about 25 μm to about 100 μm. In certain embodiments the silica and diatomaceous earth adsorbents may have an average particle size of about 400 μm to about 450 μm.

Typically, the weight ratio of activated charcoal to raw *cannabis* plant material used in preparing the cannabinoid-containing extract feed subjected to pretreatment is less than about 1:2, 1:3, 1:4, 1:5, or less than about 1:6. Typically, the weight ratio of activated charcoal to magnesium silicate and/or silica is less than about 1:1.5, 1:1.75, 1:2, or less than about 1:5. In a particular embodiment, where the adsorbent comprises a mixture of activated charcoal, magnesium silicate, and silica, a weight ratio of 2:2:1 of magnesium silicate:silica:activated charcoal is employed. In other embodiments wherein the adsorbent comprises a mixture of activated charcoal, magnesium silicate, and silica, the activated charcoal may comprise no more than about 15 wt % of the total weight of the adsorbent. For example, the activated charcoal may comprise about 12.5 wt % of the total weight of the adsorbent. In one embodiment where the cannabinoid-containing extract feed is prepared from raw *cannabis* plant material, the ratio of activated charcoal: magnesium silicate:initial raw plant mass is 1:1.5:7 on a weight basis.

The preparation of a pre-treated extract may be conducted in a continuous or batchwise manner and typically at a temperature from about 5° C. to about 50° C., from about 10° C. to about 40° C., from about 20° C. to about 40° C., from about 20° C. to about 35° C., or from about 25° C. to about 35° C. In certain embodiments, a batchwise operation is used. In embodiments where it is desirable to ensure THCA presence in the final cannabinoid-containing product, the temperature is typically from about 5° C. to about 30° C., from about 10° C. to about 30° C., from about 15° C. to about 30° C., or from about 20° C. to about 30° C.

The pre-treatment filter used to remove the particulate adsorbent from the pre-treated extract is selected to have a pore size such that it effectively removes the particulate adsorbent. In certain embodiments the pre-treatment filter may be a filter paper, filter cloth, or a combination thereof. In some embodiments, following contact with the particulate adsorbent, the pre-treated mixture may be pressurized in the pre-treatment vessel (e.g., at a pressure of from about 1 bar gauge to about 7 bar gauge) to aid in filtration of the particulate adsorbent material as it is passed through the pre-treatment filter located at the exit of the pre-treatment vessel.

In one embodiment, the pre-treated extract is prepared in a batch process and the adsorbent is contacted with the extract feed for less than about 15 minutes. It has been observed that, in some instances, longer contact and mixing time with the adsorbent may decrease the ultimate cannabinoid concentration of the final product.

Pre-treating the cannabinoid-containing extract and at least partially removing the described impurities reduces fouling of the filtration media used in the subsequent processing steps described below. This provides improved overall efficiency of the filtration media, prolonged usable-life of the filter(s), and/or the ability to produce a concentrated cannabinoid product for a commercially acceptable period of time before needing to replace or clean the process equipment.

Further, the production of a pre-treated extract reduces or eliminates the need for winterization. Winterization is a step conventionally used in the field of plant extract concentration to remove waxes, fats, chlorophyll, and other unwanted substances from the extract.

Extract Filtration:

In accordance with the present invention, a variety of separation and filtration techniques known in the art may be used in isolating desired components of the pre-treated extract to produce a concentrated cannabinoid product. Such techniques include, for example, microfiltration, ultrafiltration, nanofiltration, and reverse osmosis.

The filtration operations described herein may be performed in a batch mode or continuous mode. Examples of filter(s) particularly suitable for continuous filtration include cross-flow or tangential flow filters which may produce turbulence to move solid build up off of the element and prevent or encourage gel-layer build up (which in turn effects permeation).

The filter(s) may be configured as a single or multi-pass filter module. Additionally, the filter modules may have various geometries including flat (plate), tubular, capillary, or spiral-wound, and may be comprised of mono- or multilayered filtration media. The filter(s) or filter media are constructed of materials selected and designed to adequately withstand the prevailing conditions in the filtration operation and prolonged contact with the cannabinoid-containing extract. One skilled in the art will understand that the selection of filter media and filter configuration will have an influence on the longevity of the filter.

The filters used in the practice of the present invention are characterized by molecular weight cut-off (MWCO). MWCO values are typically defined by the manufacturer or supplier based upon the use of that filtration media in a particular filtration environment under defined conditions (e.g., an aqueous, deionized water system or sometimes another solvent system such as ethanol). However, one skilled in the art will understand that the particular composition of the material to be filtered, solvent system, temperature, and pressure may modify the observed MWCO of the filtration media when used in a system that differs from that used by the manufacturer or supplier in assigning MWCO values. Nevertheless, regardless of the composition of the pre-treated extract or other process stream to be filtered and the solvent system employed in the practice of the present invention, the MWCO values provided by the manufacturer or supplier is a suitable guide for selection of an appropriate filter in accordance with the processes described herein. That is, for example, MWCO values provided by the manufacturer or supplier for filters when used in an aqueous, deionized water system can be used to select a filter for use in the processes disclosed herein even though the composition of the pre-treated extract or other process stream may differ considerably from an aqueous, deionized water system (e.g., when processing an ethanol cannabinoid extract). When selecting a filter having a MWCO as called for in the processes disclosed herein, the value assigned by the manufacturer or supplier for the filtration environment most similar to the composition of the process stream to be treated should be used.

In several embodiments of the present invention, the filtration operation is conducted utilizing ultrafiltration or nanofiltration separation filters. Suitable ultrafiltration and nanofiltration separation filters or membranes are typically constructed of organic polymers, organic solvent stable polymers, organic nanostructures, organic solvent stable nanostructures, or ceramic materials. In certain embodiments the organic polymer separation filters may comprise polysulfone(s). In certain specific embodiments, the separation filter is constructed of an inorganic ceramic material. Certain preferred ceramic filters include, for example, filters comprising multi-channel ceramic elements on α-alumina supports, comprising $TiO_2$ layers with $TiO_2ZrO_2$ composite membrane. In certain embodiments, ceramic filters used in the present invention may comprise multiple channels (e.g., nineteen). In other embodiments, an organic solvent stable (OSS) filter may be used.

The filtration operation is typically a pressure-driven separation process driven by the difference between the operating pressure and the osmotic pressure of the solution on the feed side of the filter. The operating pressure may vary depending upon the size, type, configuration and composition of the filter that is employed. Suitable operating pressures are typically not greater than about 50 bar, not greater than about 40 bar, or not greater than about 30 bar. In certain embodiments, the filtration operation is conducted at an operating pressure of from about 10 bar to about 50 bar, from about 10 bar to about 40 bar, from about 10 bar to about 30 bar, from about 10 bar to about 25 bar, or from about 10 bar to about 20 bar. For example, in the case of tangential flow nanofiltration, the operating pressure is typically from about 15 bar to about 40 bar.

The filtration operation is typically conducted at a temperature below about 78° C. Temperatures above 78° C. may contribute to decarboxylation and a significant loss of volatile terpenes, cannabinoids, and other desirable phytoconstituents from the cannabinoid-containing extract feed. Accordingly, filtration of the cannabinoid-containing extract is suitably conducted at a temperature below about 75° C., below about 50° C., below about 40° C., or below about 30° C. In order to maintain filter integrity, the temperature is typically maintained above at least about −5° C. For example, the temperatures may be maintained above at least about 0° C., above at least about 5° C., or above at least about 10° C. For example, filtration of the cannabinoid-containing extract is suitably conducted at a temperature from about 5° C. to about 78° C., from about 5° C. to about 75° C., from about 5° C. to about 70° C., from about 5° C. to about 65° C., from about 5° C. to about 60° C., from about 5° C. to about 55° C., from about 5° C. to about 50° C., from about 5° C. to about 45° C., from about 5° C. to about 40° C., from about 10° C. to about 35° C., from about 10° C. to about 30° C., or from about 15° C. to about 25° C. However, in certain embodiments where a decarboxylated product may be desired, the filtration operation may be conducted at temperatures of 78° C. or greater.

Although some filtration processes known in the art may utilize reduced pressure (i.e. pressures below about 1 bar) for the filtration of plant extracts, in certain embodiments of the present invention the filtration operation is not performed under reduced pressure. Utilizing reduced pressures during the filtration operation of the current invention may undesirably result in the loss of volatile compounds, such as volatile terpenes.

In order to maintain or enhance separation efficiency and permeate flux, the filters should be periodically cleaned so as to remove contaminants from the surface of the filter. Suitable cleaning includes cleaning-in-place (CIP) operations wherein the surface of the membrane is exposed to a cleaning solution while installed. Preferred systems monitor the component concentration of the retentate, and/or permeate and/or the permeate flux to determine if cleaning is needed. Cleaning protocols and cleaning solutions may vary depending on the type of separation filter employed and are generally available from the filter manufacturer. Suitable cleaning solutions may include, for example, caustic or alkaline solutions. In order to not damage the filters and unnecessarily shorten filter life, the CIP operation is preferably conducted using a solution of a standard pH at pressure and temperature conditions known to those skilled in the art. In some applications, it may be advantageous to conduct a cleaning operation on new filters prior to use in the filter separation operation in order to improve filter performance.

First or Single Filtration Stage:

The pre-treated extract is contacted with a first filter to produce a first retentate and a first permeate. The first retentate comprises large molecular weight impurities and the first permeate comprises cannabinoids. In addition to cannabinoids, the first permeate may also comprise flavonoids, terpenes and/or other desirable phytoconstituents.

The first filter typically has a molecular weight cut-off (MWCO) such that the large molecular weight impurities are substantially rejected and removed from the cannabinoid-containing permeate and the concentration of cannabinoids in the first permeate is higher than the concentration of cannabinoids in the first retentate. Suitable filters for use in the first filter stage have a MWCO of from about 400 daltons to about 5,000 daltons, from about 500 daltons to about 4,000 daltons, from about 600 daltons to about 3,000 daltons, from about 700 daltons to about 2,000 daltons, from about 800 daltons to about 1,500 daltons, from about 900 daltons to about 1,250 daltons, or from about 900 daltons to about 1,100 daltons. In certain other embodiments the first filter has a MWCO of from about 1,000 daltons to about 5,000 daltons.

Separation filters for use in the first or single filter stage may be constructed from the materials noted above, including organic polymers and inorganic ceramic materials. Suitable materials of construction include, for example and without limitation, filters comprising a crosslinked thin film composite layer on a polyethylene terephthalate non-woven sublayer, a spacer polypropylene, and polyamide. Filters of this composition are pH stable when subjected to a pH of no greater than about 14. Additional filters may comprise a thin film composite layer on a polyethylene terephthalate non-woven sublayer, a spacer polypropylene, and polyamide.

Examples of suitable separation filters for use in the first or single filter stage include, for example and without limitation, Synder NFG, Synder XT, Synder MT, and Synder VT produced by Synder Filtration, Inc. (Vacaville, Calif.), GE Osmonics UF GK, GE Osmonics UF GH, GE Osmonics UF PT, and GE Osmonics UF GE available from Sterlitech Corporation (Kent, Wash.), TriSep UF UA60, TriSep NF XN45, and TriSep NF TS40 produced by TriSep Corporation (Goleta, Calif.), and Dow Filmtec NF produced by Dow Chemical Company (Midland, Mich.). Examples of suitable organic solvent stable (OSS) filters for use as the first filter include, SolSep UF10706, SolSep UF03705, and SolSep NF080105 produced by SolSep BV (St. Eustatius, Netherlands), and Novamem PVDF20 and Novamem PEEK 1000 produced by Novamen Ltd. (Schlieren, Switzerland).

Examples of suitable ceramic separation filters for use in the first or single filter stage include, for example and without limitation, a 500 to 800 dalton MWCO ceramic filter; a 400 dalton MWCO ceramic filter comprising 19 channels, having a length of 1000 mm, and an inner diameter of 3.3 mm; a 500 dalton MWCO ceramic filter comprising 1 channel, having a length of 500 mm, and an inner diameter of 6.0 mm; a 600 dalton MWCO ceramic filter comprising 19 channels, having a length of 117.5 mm, and an inner diameter of 3.3 mm; a 750 dalton MWCO ceramic filter comprising 19 channels, having a length of 1000 mm, and an inner diameter of 3.3 mm; a 750 dalton MWCO ceramic filter comprising 1 channel, having a length of 500 mm, and an inner diameter of 6.0 mm; a 800 dalton MWCO ceramic filter comprising 19 channels, having a length of 117.5 mm, and an inner diameter of 3.3 mm; a 850 dalton MWCO ceramic filter comprising 1 channel, having a length of 500 mm, and an inner diameter of 6.0 mm; and a 900 dalton MWCO ceramic filter comprising 1 channel, having a length of 500 mm, and an inner diameter of 6.0 mm.

For certain filter materials (e.g., ethanol sensitive, such as OSS filters), the solvent from the cannabinoid-containing extract feed may reduce the usable life of the filter and increase overall process costs. Accordingly, in certain embodiments, water may be added to the pre-treated extract before contact with the first filter in an amount sufficient to reduce the concentration of solvent originating from the pre-treated extract feed. For example, water may be added in a proportion sufficient to reduce the solvent content in the extract to less than about 80 wt %, less than about 75 wt %, less than about 70 wt %, or less than about 65 wt %. Where water is added to the pre-treated extract stream or other process streams in the practice of the present invention, deionized water is typically used. Whether or not water is added to the pre-treated extract stream or other process streams, the process streams typically have a water content such that the stream is maintained below its cloud point. At the cloud point, process streams may form an oil that can affect the processing ability of the equipment, and ultimately result in reduced overall cannabinoid concentration in the final product.

The filtration operation of the first filter stage is typically conducted at a temperature of from about 5° C. to about 50° C., from about 10° C. to about 50° C., from about 20° C. to about 50° C., or from about 25° C. to about 50° C. In certain other embodiments, the filtration operation of the first filter stage is typically conducted at a temperature of from about 20° C. to about 25° C.

In one embodiment, the first permeate is collected and subjected to the filtrate extraction step detailed below. In other embodiments, the first permeate is contacted with a second filter in a second filter stage. The first retentate may be recycled to the process for further filtration, collected as a waste product, or otherwise processed before disposal.

In certain other embodiments an enhanced concentrated cannabinoid product may be obtained using only a single filter stage. It has been surprisingly found that an unexpectedly high recovery of cannabinoids can be attained by increasing the water content of the first permeate and recycling the water-adjusted first permeate to the first stage filter. In one embodiment wherein the water content of the first permeate is increased and the water-adjusted first permeate is recycled to the first stage, the first filter stage comprises a ceramic filter. For example, the water content of the first permeate recovered from the first filter in the first filter stage is adjusted to between about 20 wt % and about 40 wt % and recycled to the first filter stage. For example, the water content may be adjusted to between about 22 wt % and about 38 wt % between about 24 wt % and about 36 wt %, between about 26 wt % and about 36 wt %, between about 28 wt % and about 36 wt %, or between about 28 wt % and about 35 wt %. It is believed that the increased water content in the first permeate recycled to the first filter stage causes aggregation of molecules in the first permeate such that a second exposure to the first filter removes a substantial portion of lower molecular weight components not usually anticipated to be removed when using a filter having a MWCO of from about 400 daltons to about 5,000 daltons. While most lower molecular weight components such as cannabinoids, terpenes and other desirable phytoconstituents pass through the first stage filter as components of the first permeate, by adjusting the water content of the first permeate recycled to the first filter, a substantial portion of these components are separated in the second retentate produced from the recycled first permeate and a substantial portion the extract solvent is present in the resulting permeate. Operation of the first filter stage in this manner allows for a reduced number of filters to be used and consequently decreases the cost associated with maintaining, cleaning, repairing, and replacing multiple filters. A concentrated cannabinoid product may be recovered from the cannabinoid-containing retentate produced from the recycled first permeate as described in further detail below.

In certain embodiments of the first or single filtration stage, at least about 75% by weight of compounds having a molecular weight greater than about 500 daltons contained in the pre-treated extract are retained in the first retentate. In another embodiment of the first or single filtration stage, at least about 80% by weight of compounds having a molecular weight greater than about 500 daltons contained in the pre-treated extract are retained in the first retentate. In yet another embodiment of the first or single filtration stage, at least about 85% by weight of compounds having a molecular weight greater than about 500 daltons contained in the pre-treated extract are retained in the first retentate. In a further embodiment of the first or single filtration stage, about 75-85% by weight of compounds having a molecular weight greater than about 500 daltons contained in the pre-treated extract are retained in the first retentate.

Second Filtration Stage:

In several embodiments of the present invention, the first permeate produced in the first filter stage is contacted with a second filter to produce a second retentate and a second permeate. The second retentate comprises cannabinoids, while the second permeate comprises small molecular weight impurities present in the first permeate. In addition to cannabinoids, the second retentate may comprise flavonoids, terpenes and/or other desirable phytoconstituents present in the first permeate produced in the first filter stage.

The second filter may be a filter having a molecular weight cut-off (MWCO) such that the small molecular weight impurities are substantially removed from the cannabinoid-containing second retentate and the concentration of the cannabinoids in the second retentate is higher than the concentration of cannabinoids in the second permeate. Suitable filters for use in the second filter stage have a MWCO of from about 150 daltons to about 1,000 daltons, from about 150 daltons to about 900 daltons, from about 150 daltons to about 800 daltons, from about 150 daltons to about 700 daltons, from about 150 daltons to about 600 daltons, from about 150 daltons to about 500 daltons, from about 150 daltons to about 400 daltons, from about 200 daltons to about 400 daltons, from about 250 daltons to about 400 daltons, or from about 300 daltons to about 400 daltons.

Separation filters for use in the second filter stage may be constructed from the materials noted above, including organic polymers and inorganic ceramic materials. Suitable materials of construction include, for example and without limitation, filters comprising a crosslinked thin film composite layer on a polyethylene terephthalate non-woven sublayer, a spacer polypropylene, and polyamide. Filters of this composition are pH stable when subjected to a pH of no greater than about 14. Additional filters may comprise a thin film composite layer on a polyethylene terephthalate non-woven sublayer, a spacer polypropylene, and polyamide.

Examples of suitable separation filters for use as the second filter include, for example and without limitation, Synder NFG, Synder XT, and Synder NFX produced by Synder Filtration, Inc. (Vacaville, Calif.), GE Osmonics UF GE, GE Osmonics UF Duracid, and GE Osmonics UF DK available from Sterlitech Corporation (Kent, Wash.), TriSep NF TS80 and TriSep NF XN45 produced by TriSep Corporation (Goleta, Calif.), Dow Filmtec NF produced by Dow Chemical Company (Midland, Mich.), and Nanostone NF NF4 and Nanostone NF NF8 produced by Nanostone Water Inc. (Eden Prairie, Minn.). Examples of suitable organic solvent stable (OSS) filters for use as the second filter include, SolSep NF090801, SolSep NF03705, SolSep SR1 NF080105, SolSep UF10706, SolSep UF03705, SolSep NF08105, and SolSep NF10706 produced by SolSep BV (St. Eustatius, Netherlands), and Novamem PVDF20 and Novamem PEEK 1000 produced by Novamen Ltd. (Schlieren, Switzerland).

Further examples of suitable separation filters for use as the second filter include filters comprising a crosslinked composite layer on a polyethylene terephthalate non-woven sublayer, a spacer polypropylene, and polyamide. Filters of this composition may be pH stable when subjected to a pH of no greater than about 14. Additional filters may include filters comprising a composite layer on a polyethylene terephthalate non-woven sublayer, a spacer polypropylene, and polyamide.

According to some embodiments, the second filter does not comprise a ceramic filter.

In some embodiments, the conditions of the filtration operation in the second filter stage are substantially similar to that of the first filter stage.

In other embodiments of the present invention, the second filter stage may be operated with the addition of water to the first permeate prior to contact with the second filter. In several embodiments, the first permeate may have an initial water content from about 0.5 wt % to about 6 wt %, from about 0.75 wt % to about 5.5 wt %, from about 1 wt % to about 5 wt %, from about 1.25 wt % to about 4.75 wt %, from about 1.5 wt % to about 4.5 wt %, from about 1.75 wt % to about 4.25 wt %, or from about 2 wt % to about 4 wt %. The addition of water allows for additional permeate to be generated at a set pressure, due to a reduction in the osmotic pressure of the feed stream. As additional second permeate is generated, transmission of components through the second filter for which the filter demonstrates a low rejection also increases. For example, when the concentration of cannabinoids in the cannabinoid-containing first permeate process stream is lower than the concentration of low molecular weight impurities, the addition of water may increase passage of low molecular weight impurities through the second filter, due to the additional water transmission through the filter and the relatively low rejection characteristic of the filter with respect to the low molecular weight impurities. In this manner, the addition of water may be employed to assist in the recovery of a second retentate comprising the desired cannabinoids and having a higher concentration of cannabinoids relative to the second permeate. Typically, in operations comprising an addition of water to the first permeate, the water content of the first permeate is increased to between about 15 wt % and about 35 wt %, between about 20 wt % and about 30 wt %, or between about 25 wt % and about 30 wt %. The second permeate may be recycled to the process for further filtration, collected as a waste product, or otherwise processed before disposal.

In certain embodiments of the second filtration stage, at least about 75% by weight of compounds having a molecular weight less than about 200 daltons contained in the first permeate are transferred to the second permeate. In another embodiment of the second filtration stage, at least about 80% by weight of compounds having a molecular weight less than about 200 daltons contained in the first permeate are transferred to the second permeate. In yet another embodiment of the second filtration stage, at least about 85% by weight of compounds having a molecular weight less than about 200 daltons contained in the first permeate are transferred to the second permeate. In a further embodiment of the second filtration stage, about 75-85% by weight of compounds having a molecular weight less than about 200 daltons contained in the first permeate are transferred to the second permeate.

Filtrate Extraction and Recovery of a Concentrated Cannabinoid Product:

In embodiments where only a first filter is used, a concentrated cannabinoid product is recovered from the first permeate. In embodiments where a single filter is used as the first filter and a water-adjusted first permeate is recycled, a concentrated cannabinoid product is recovered from the second retentate. In embodiments where a first filter and a second filter are used, a concentrated cannabinoid product is recovered from the second retentate. One skilled in the art will understand that the composition of the first permeate or second retentate will depend upon a variety of factors including the composition of the cannabinoid-containing extract feed.

In one embodiment, the first permeate or second retentate is combined with an extractant in an extraction vessel to form a filtrate extraction mixture comprising an extract phase comprising cannabinoids, and optionally flavonoids, terpenes and/or other desirable phytoconstituents and a raffinate phase comprising solvent from the cannabinoid-containing extract feed.

Suitable extractants include, but are not limited to, medium-chain triglyceride (MCT) oil, palm kernel oil, coconut oil, olive oil, sesame seed oil, almond oil, grape seed oil, hemp seed oil, and mixtures thereof. In certain embodiments, the extractant may be combined with an aqueous brine solution. In one embodiment, a 50% brine solution and an oil extractant (e.g., MCT oil) are added to the extraction vessel. A 50% brine solution will be understood by one skilled in the art to mean a half saturated brine (i.e. a solution containing approximately 16 wt % brine). The use of a brine solution aids in separation of the layers and recovery of the cannabinoid-containing phase. When using brine, the extractant (for example MCT oil) will separate on top as the extract phase, while the brine solution separates on the bottom as the raffinate phase. This reduces processing time and cost, and also allows for an easier separation of the cannabinoid rich extract phase. It has also been observed that the use of brine reduces the occurrence of emulsions in the filtrate extraction mixture. The volumetric ratio of brine solution to extractant can vary considerably. Typically, the volumetric ratio of brine solution to extractant is from about 1:1 to about 2:1.

Typically, the extraction is carried out at a temperature of less than about 25° C., less than about 20° C., less than about 20° C., less than about 10° C., less than about 15° C., less than about 5° C., or less than about 0° C. For example, from about 25° C. to about −20° C., from about 20° C. to about −20° C., from about 15° C. to about −20° C., from about 10° C. to about −20° C., from about 5° C. to about −15° C., or from about 0° C. to about −10° C. Typically, the extraction is carried out at a pressure of at least about 1 bar, at least about 2 bar, at least about 3 bar, at least about 4 bar, or at least about 5 bar. For example, from about 1 bar to about 10 bar, from about 1 bar to about 9 bar, from about 1 bar to about 8 bar, from about 1 bar to about 7 bar, or from about 1 bar to about 6 bar. After a suitable contact time within the extraction vessel, the extract phase (comprising the extractant, cannabinoids and other desirable phytoconstituents) is removed from the vessel as the concentrated cannabinoid product and may be optionally subjected to additional processing. The raffinate phase comprising solvent from the cannabinoid-contacting extract feed and may be recycled to previous steps of the process for further processing (for example, contacted again with an extractant in the extraction vessel), collected as a waste product, or otherwise processed before disposal.

The extract phase comprising cannabinoids may be transferred to a recovery vessel and combined with a drying agent to reduce the water content of the product. Suitable drying agents may be selected from the group consisting of metal salts (e.g., NaCl, $MgSO_4$, $Na_2SO_4$, $CaCl_2$, and $CaSO_4$), alumino silicates (e.g., a 3-5 Å molecular sieve), and combinations thereof. After a suitable contact time, the dried extract phase is passed through a filter (e.g., a polytetrafluoroethylene (PTFE) membrane filter) to remove the drying agent and recover a concentrated cannabinoid product. In one embodiment, the PTFE membrane filter may have an average pore size of about 0.45 μm. In another embodiment the dried extract phase may be passed through the filter under nitrogen pressure.

In a further embodiment, the extraction is carried out by subjecting the first permeate or second retentate to an extractant. In certain embodiments, the volumetric ration of water to extractant is about 2:1. After a period of time an oil phase, comprising the cannabinoid-containing product, and aqueous phase will form. The oil phase may be separated from the aqueous phase by methods known in the art, for example subjecting the extraction mixture to centrifugal force. The oil phase may be physically separated from the remaining aqueous phase and utilized as the concentrated cannabinoid-containing product.

Recovering a Concentrated Cannabinoid Product without Filtrate Extraction

In certain embodiments a concentrated cannabinoid product may be recovered from the first permeate or the second retentate without use of an extractant. For example, the first or second permeate may be transferred to an evaporator and heated to remove solvent and obtain a concentrated cannabinoid product in the form of a semi-solid oil deposit. In such an alternative embodiment, first permeate or second retentate may be transferred to a rotary evaporator or similar device wherein the solvent is removed and the semi-solid oil deposit generated within the evaporator vessel is collected as the concentrated cannabinoid product.

Examples of suitable rotary evaporators include a R-Series Rotavapor produced by BÜCHI Labortechnik AG (Flawil, Switzerland), Labtech EV311 produced by LabTech, Inc. (Hopkinton, Mass.), or RE-Series EcoVap produced by Hydrion Scientific Instruments Co., Ltd. (Baltimore, Md.). Typical temperatures for the evaporative recovery of a concentrated cannabinoid product in the form of a semi-solid oil deposit are from about 10° C. to about 50° C., from about 15° C. to about 45° C., from about 20° C. to about 40° C., from about 25° C. to about 35° C., or from about 25° C. to about 30° C. Typical pressures for the evaporative recovery of a concentrated cannabinoid product in the form of a semi-solid oil deposit are from about −2 bar to about 2 bar, from about −1 bar to about 1 bar, or from about −1 bar to about 0.6 bar.

Concentrated Cannabinoid Product Analysis

As will be understood by one skilled in the art, and depending upon the intended use of the concentrated cannabinoid product, the concentrated cannabinoid product may be analyzed to determine the content of particular cannabinoids, terpenes, flavonoids, or other phytoconstituents of interest. Suitable methods of analysis are well-known to those skilled in the art. One such method is the use of high performance liquid chromatography (HPLC).

The process for the present invention typically results in a concentrated cannabinoid product comprising at least about 30 wt %, at least about 40 wt %, at least about 50 wt %, at least about 60 wt %, at least about 65 wt %, at least about 70 wt %, at least about 75 wt %, at least about 80 wt %, at least about 85 wt %, at least about 90 wt %, at least about 92 wt %, or at least about 95 wt % cannabinoids.

Additionally, the process of the present invention typically results in a total cannabinoid loss, as defined by (total weight of cannabinoids in the cannabinoid-containing extract feed)−(total weight of cannabinoids in concentrated cannabinoid product)/(total weight of cannabinoids in cannabinoid-containing extract feed), of less than about 20%, less than about 15%, less than about 10%, less than about 5%, less than about 2%, or less than about 1%.

In certain embodiments, a concentrated cannabinoid product comprising from about 30 wt % to about 40 wt % cannabinoids may be obtained from a cannabinoid-containing extract feed comprising about 5 wt % cannabinoids.

Many procedures for determining the concentration of cannabinoids in the concentrated cannabinoid product may be used. One such method comprises utilizing a purchased standard containing about 1 mg/ml of cannabinoids and diluting the standard to a concentration of about 0.75 mg/ml, about 0.5 mg/ml, about 0.25 mg/ml, about 0.1 mg/ml, about 0.05 mg/ml, about 0.04 mg/ml, about 0.02 mg/ml, or about 0.01 mg/ml. The standard containing cannabinoids many comprise any number of cannabinoids such as THC, THCA, CBD, CBDA, CBN, CBG, CBGA, CBC, CBCA, and THCV. The resulting analysis of the standard containing cannabinoids may then be plotted for each cannabinoid present, and a correlation between observed peak area and concentration on a mass basis may be calculated. Thereafter, the concentrated cannabinoid product may be subjected to the same analysis in which the observed peak area is correlated to a concentration of cannabinoids on a mass basis. Examples of suitable cannabinoid-containing standards comprising cannabinoids such as THC, THCA, CBD, CBDA, CBN, CBG, CBGA, CBC, CBCA, and THCV include standards produced by Cerilliant Corporation (Round Rock, Tex.).

One procedure for determining the concentration of terpenes in the concentrated cannabinoid product involves utilizing a standard containing 2.5 mg/ml of terpene compounds and diluting the standard to about 1.25 mg/ml, about 0.625 mg/ml, about 0.25 mg/ml, or about 0.125 mg/ml. Thereafter, the concentration on a weight basis may be correlated to the observed peak area as discussed above. Suitable terpene standards, for example a standard containing 20 terpenes, include those produced by Restek Corporation (Bellefonte, Pa.).

Another procedure for determining the presence of certain terpenes in the concentrated cannabinoid product (as opposed to the concentration of terpenes) involves utilizing a standard containing about 100 µm/ml terpenes. The terpene containing standard is analyzed and the location of terpene peaks are noted. Thereafter, the concentrated cannabinoid product is analyzed and the variation in height of the specific peaks over time may be used as an indicator of the presence of the certain terpenes identified in the standard. Suitable terpene standards for use in qualitative analysis of the concentrated cannabinoid product include those produced by SPEX CertiPrep Inc. (Metuchen, N.J.).

One procedure for testing for the presence of certain flavonoids in the concentrated cannabinoid product involves solubilizing a powder or dry standard containing apigenin, luteolin, and/or kaempferol in ethanol or methanol. The resulting solution is analyzed and the locations of flavonoid peaks are noted. Thereafter, the concentrated cannabinoid product is analyzed and the variation in height of the specific peaks and the time at which peaks occur may be used as an indicator of the presence of the certain flavonoids. Suitable powder flavonoid standards include those produced by Sigma-Aldrich Co. (St. Louis, Mo.).

The following non-limiting examples are provided to further illustrate the present invention.

EXAMPLES

Example 1: A Process Utilizing a First and a Second Filter

As set forth in FIG. 1, *cannabis* plant material 2 is contacted with ethanol stream 4, at a ratio of 25 ml of ethanol per gram of raw *cannabis*, and a grinding media 6 comprising zirconia grinding balls, at a weight ratio of 1:1 (zirconia grinding balls:raw *cannabis*), in extraction vessel 8. Mixing is performed in extraction vessel 8 until a fine brown powder forms.

After ensuring that stream 10 contains a water content of less than 95 wt %, stream 10 is combined with an adsorbent 12 comprising FLORISIL, silica, and charcoal in a ratio of 2:2:1 in a pre-treatment vessel 14. The silica used is Sili-Cycle UltraPure (approximate particle size 40 mesh). The charcoal used is decolorizing activated charcoal obtained from Sigma-Aldrich Co. (approximate particle size 100 mesh). The FLORISIL used is from Sigma-Aldrich Co., having a particle size of approximately 100 mesh. The contents of the pre-treatment vessel are mixed for less than about 15 minutes before being pressurized and passed through filter 16 in stream 18. Filter 16 is a 11 µm filter.

At a flow rate of 6 L/min, stream 18 is contacted with first filter 20 at a temperature from about 10-25° C. and a pressure of about 20-30 bar. First filter 20 has a MWCO of from about 400 to about 5,000 daltons. First retentate 22 is removed as waste. Optionally, at least a portion of first retentate 22 may be combined with stream 18, via stream 24, and contacted with first filter 20 for further filtering. The first permeate is removed from first filter 20 via stream 26. First permeate 26 contains a higher concentration of cannabinoids than first retentate 22.

First permeate 26 is then contacted with second filter 28 at a temperature from about 10-25° C. and a pressure of about 20-30 bar. First permeate 26 may optionally be adjusted to have a water content of from about 28 wt % to about 34 wt % using a water stream 32. Second filter 28 has a MWCO of from about 150 to about 1,000 daltons, and produces a second retentate 38 and second permeate 34. The second retentate 38 is removed from second filter 28 when the concentration of cannabinoids present in second retentate 38 is at least about 30 mg per milliliter of retentate. For purposes of this measurement, the cannabinoids THC, THCA, and CBD are used in determining cannabinoid concentration. Second permeate 34 may be removed as waste. Optionally, at least a portion of second permeate 34 may be combined with stream 26, via stream 36, and contacted with second filter 28 for further filtering. Optionally, a water stream 30 may be combined with first permeate 26 to ensure that more impurities are removed from the second retentate 38.

Second retentate 38 is then combined with an extractant stream 40 in the extractant vessel 42. MCT oil from stream 40 is combined with second retentate 38 and mixed until a homogeneous mixture is formed. A 50% brine solution is then added. The MCT oil and 50% brine solution added to the extractant vessel 42 comprises a 2:1 ratio of 50% brine to MCT oil. The MCT oil layer is removed from extractant vessel 42 as stream 44. The remaining contents of the extractant vessel 42 are removed via stream 46 and removed as waste. Optionally, at least a portion of stream 46 may be combined with stream 38 via stream 48 for further processing.

The MCT oil layer stream 44 is contacted with a drying agent 50 in recovery vessel 52. The contents of recovery vessel 52 are then pressurized using nitrogen and passed through a 0.45 µm PTFE filter. The final product is collected in stream 54 as the concentrated cannabinoid product. Stream 54 may be analyzed to determine the relative amounts of cannabinoids, terpenes, flavonoids, etc.

Example 2: A Process Utilizing a First Filter

Figure 2:
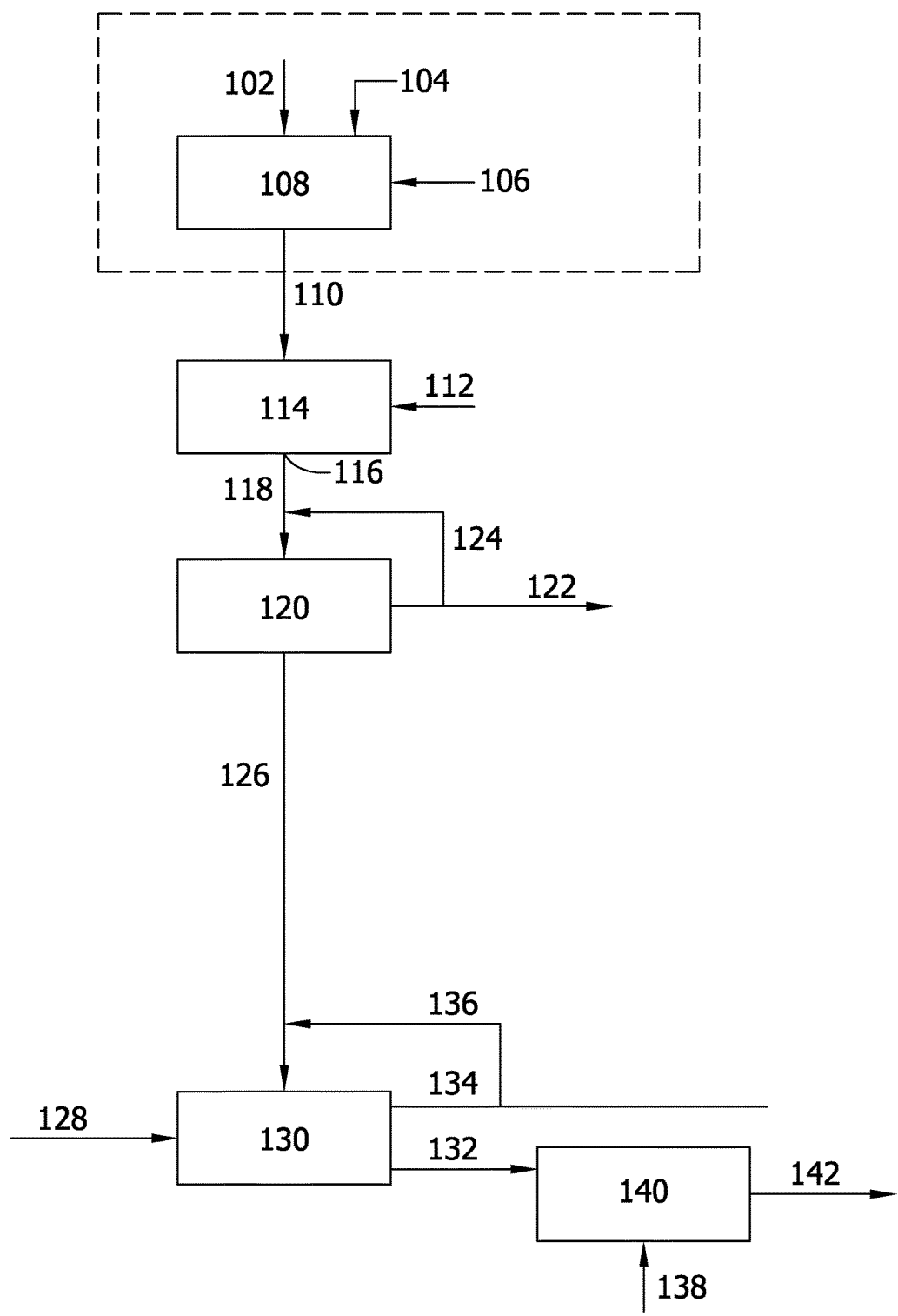
FIG. 2 shows the process flow schematic of a process for the production of a concentrated cannabinoid product wherein a first filter is used.

As set forth in FIG. 2, *cannabis* plant material 102 is contacted with an ethanol stream 104, at a ratio of 25 ml of ethanol per gram of raw *cannabis*, and a grinding media 106 comprising zirconia grinding balls, at a weight ratio of 1:1 (zirconia grinding balls:raw *cannabis*), in extraction vessel 108. Mixing is performed in extraction vessel 108 until a fine brown powder forms.

After ensuring that stream 110 contains a water content of less than 95 wt %, stream 110 is combined with an adsorbent 112 comprising FLORISIL, silica, and charcoal in a ratio of 2:2:1, in pre-treatment vessel 114. The silica used is Sili-Cycle UltraPure (approximate particle size 40 mesh). The charcoal used is decolorizing activated charcoal obtained from Sigma-Aldrich Co. (approximate particle size 100 mesh). The FLORISIL used is from Sigma-Aldrich Co., having a particle size of approximately 100 mesh. The contents of the pre-treatment vessel are mixed for less than about 15 minutes before being pressurized and pass through filter 116 as stream 118. Filter 116 is a 11 µm filter.

At a flow rate of 6 L/min, stream 118 is contacted with first filter 120 at a temperature from about 20-25° C. and a pressure of about 20-30 bar. First filter 120 has a MWCO of from about 400 to about 5,000 daltons. First retentate 122 is removed as waste. Optionally, at least a portion of first retentate 122 may be combined with stream 118, via stream 124, and contacted with first filter 120 for further filtering. First permeate 126 is removed from first filter 120. First permeate 126 contains a higher concentration of cannabinoids than first retentate 122.

First permeate 126 is then combined with extractant stream 128 in the extractant vessel 130. Stream 128 is combined with first permeate 126 and mixed until a homogeneous mixture is formed. A 50% brine solution is then added. The MCT oil and 50% brine solution added to the extractant vessel 130 comprises a 2:1 ratio of 50% brine to MCT oil. The MCT oil layer is removed from extractant vessel 130 as stream 132. The remaining contents of the extractant vessel are removed via stream 134 and removed as waste. Optionally, at least a portion of stream 134 may be combined with stream 126, via stream 136, for further processing.

The MCT oil layer stream 132 is contacted with a drying agent 138 in recovery vessel 140. The contents of recovery vessel 140 are then pressurized and passed through a 0.45 μm PTFE filter. The final product is collected in stream 142 as the concentrated cannabinoid product. Stream 142 may be analyzed to determine the relative amounts of cannabinoids, terpenes, flavonoids, etc.

Example 3: A Process Utilizing a First Filter

Figure 3:
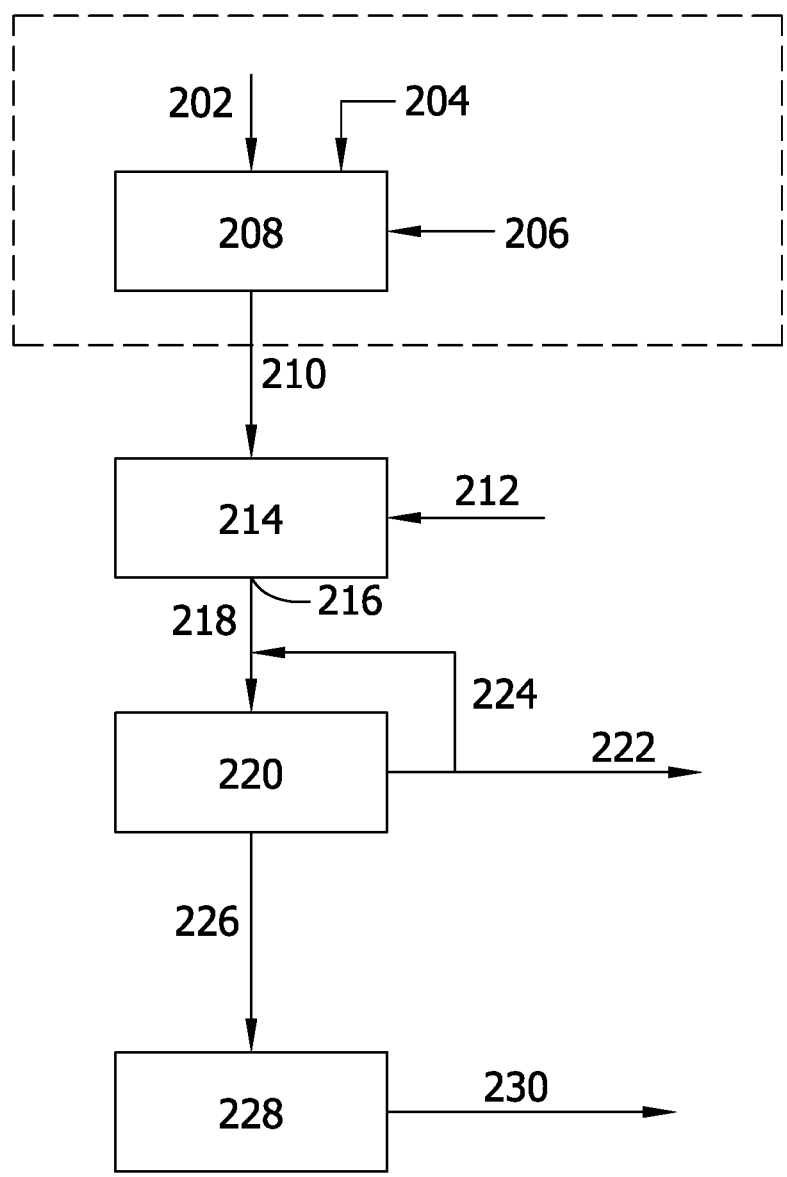
FIG. 3 shows the process flow schematic of a process for the production of a concentrated cannabinoid product wherein a first filter and a rotary evaporator are used.

As set forth in FIG. 3, the *cannabis* plant material 202 is contacted with ethanol stream 204, at a ratio of 25 ml of ethanol per gram of raw *cannabis*, and a grinding media 206 comprising zirconia grinding balls, at a weight ratio of 1:1 (zirconia grinding balls:raw *cannabis*), in an extraction vessel 208. Mixing is performed in the extraction vessel 208 until a fine brown powder forms.

After ensuring that stream 210 contains a water content of less than 95 wt %, stream 210 is combined with an adsorbent 212 comprising FLORISIL, silica, and charcoal in a ratio of 2:2:1. The silica used is SiliCycle UltraPure (approximate particle size 40 mesh). The charcoal used is decolorizing activated charcoal obtained from Sigma-Aldrich Co. (approximate particle size 100 mesh). The FLORISIL used is from Sigma-Aldrich Co., having a particle size of approximately 100 mesh. The resulting solution is mixed in pre-treatment vessel 214 for less than about 15 minutes before being pressurized and passed through filter 216 as stream 218. Filter 216 is a 11 μm filter.

At a flow rate of 6 L/min, stream 218 is contacted with first filter 220 at a temperature from about 20-25° C. and a pressure of about 20-30 bar. First filter 220 has a MWCO of from about 400 to about 5,000 daltons. First retentate 222 is removed as waste. Optionally, at least a portion of first retentate 222 may be combined with stream 218 via stream 224 and contacted with first filter 220 for further filtering. First permeate 226 is removed from first filter 220. First permeate 226 contains a higher concentration of cannabinoids than first retentate 222.

First permeate 226 is then transferred to rotary evaporator 228. First permeate 226 is subjected to the rotary evaporation until a semi-solid oil deposit is generated. The deposit is then removed from rotary evaporator 228 as stream 230. Stream 230 comprises the concentrated cannabinoid product. Stream 230 may be analyzed to determine the relative amounts of cannabinoids, terpenes, flavonoids, etc.

Example 4: Evaluation of a Molecular Weight Cut-Off Filter

Figure 4:
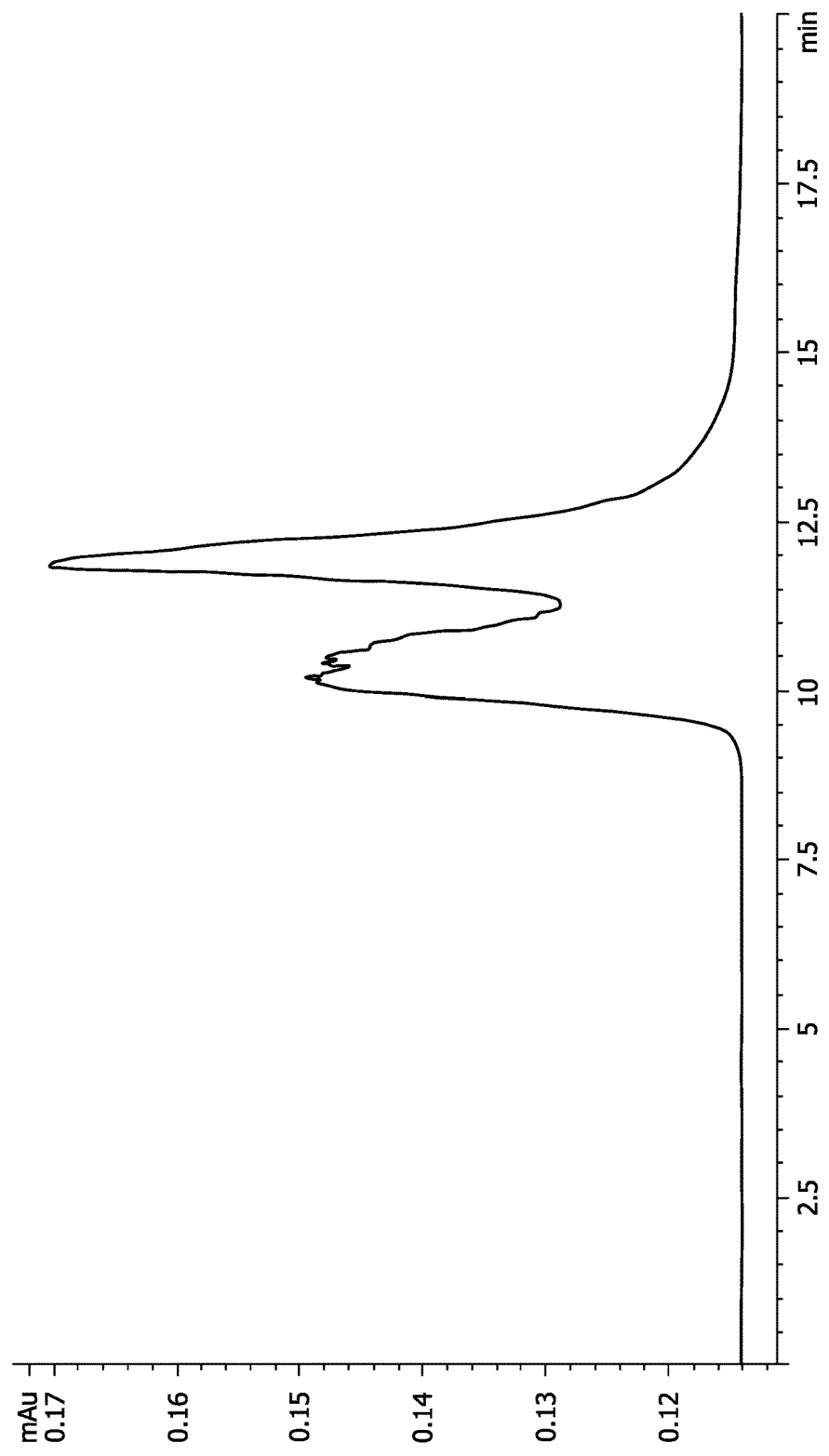
FIG. 4 shows the molecular weight analysis of a representative pre-treated extract stream subjected to size exclusion chromatography.

FIG. 4 shows the initial molecular weight population of a representative pre-treated extract stream. Materials having a weight of 1,100 daltons were observed at approximately 11 minutes when subjected to size exclusion chromatography, whereas higher molecular weight materials were observed at about 10 minutes. One skilled in the art will understand size exclusion chromatography to typically involve the use of an adsorbent or stationary phase that allows larger molecular weight objects to pass through the phase relatively quickly, while smaller molecular weight objects take a longer time to pass through the adsorbent. This phenomenon is observed due to the large molecular weight objects being too large to enter the pores of the adsorbent, and therefore bypassing the pores. On the other hand, small molecular weight objects are capable of entering the pores of the adsorbent, and thus take a longer period of time to pass through and be observed at the exit of the stationary phase. Suitable standards for testing the molecular weight cut-off of filters, for example polystyrene based polymers, may be obtained from Sigma-Aldrich Co. (St. Louis, Mo.) or PSS Polymer Standards Service GmbH (Mainz, Germany).

Figure 5:
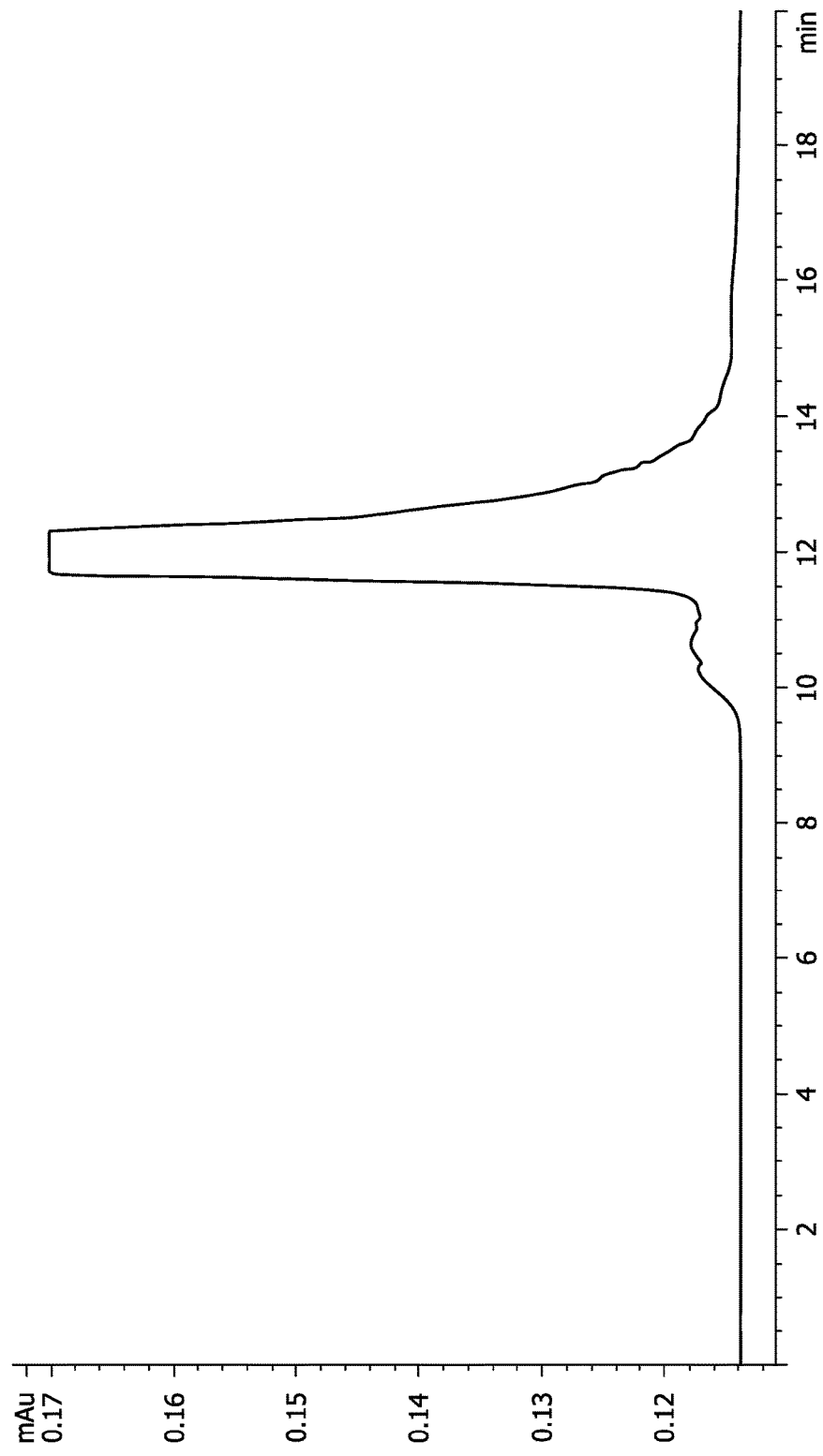
FIG. 5 shows the molecular weight analysis of the permeate of the solution of FIG. 4 after contact with a filter having a MWCO of 1000 daltons.

It can be seen in FIG. 5 that after the pre-treated extract stream was contacted via tangential flow with a 1,100 dalton MWCO ceramic filter comprising 19 channel ceramic elements on α-alumina support, comprising $TiO_2$ layers with $TiO_2ZrO_2$ composite the higher molecular weight materials were no longer present in the stream.

The results of this example demonstrate that the 1,100 MWCO filter effectively removes high molecular weight materials and exhibits a rejection in accordance with its 1,100 dalton molecular weight design.

Example 5: Treatment of a THCA Rich Stream

Figure 6:
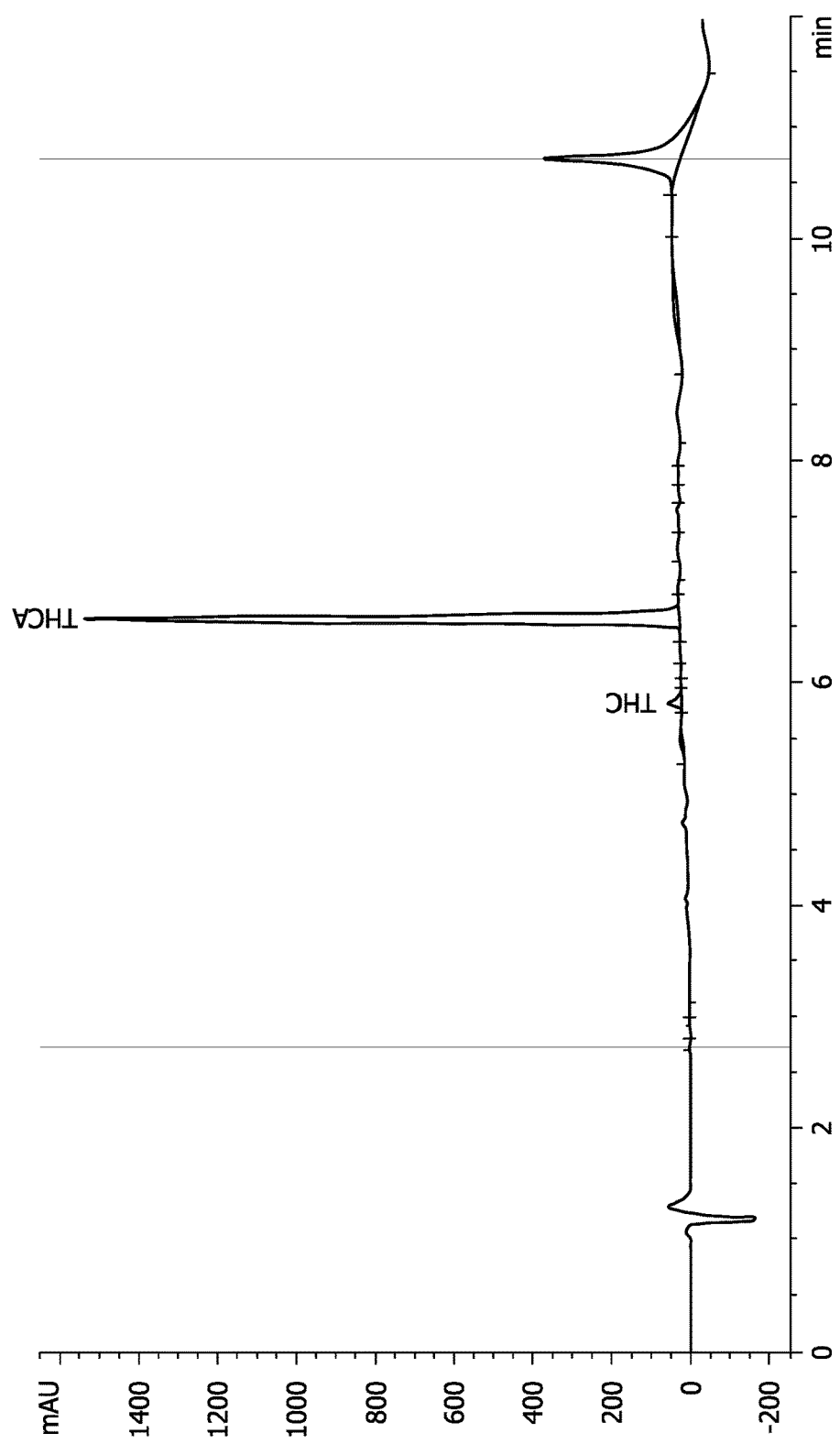
FIG. 6 shows the chromatography analysis of a THCA rich pre-treated extract stream.
Figure 7:
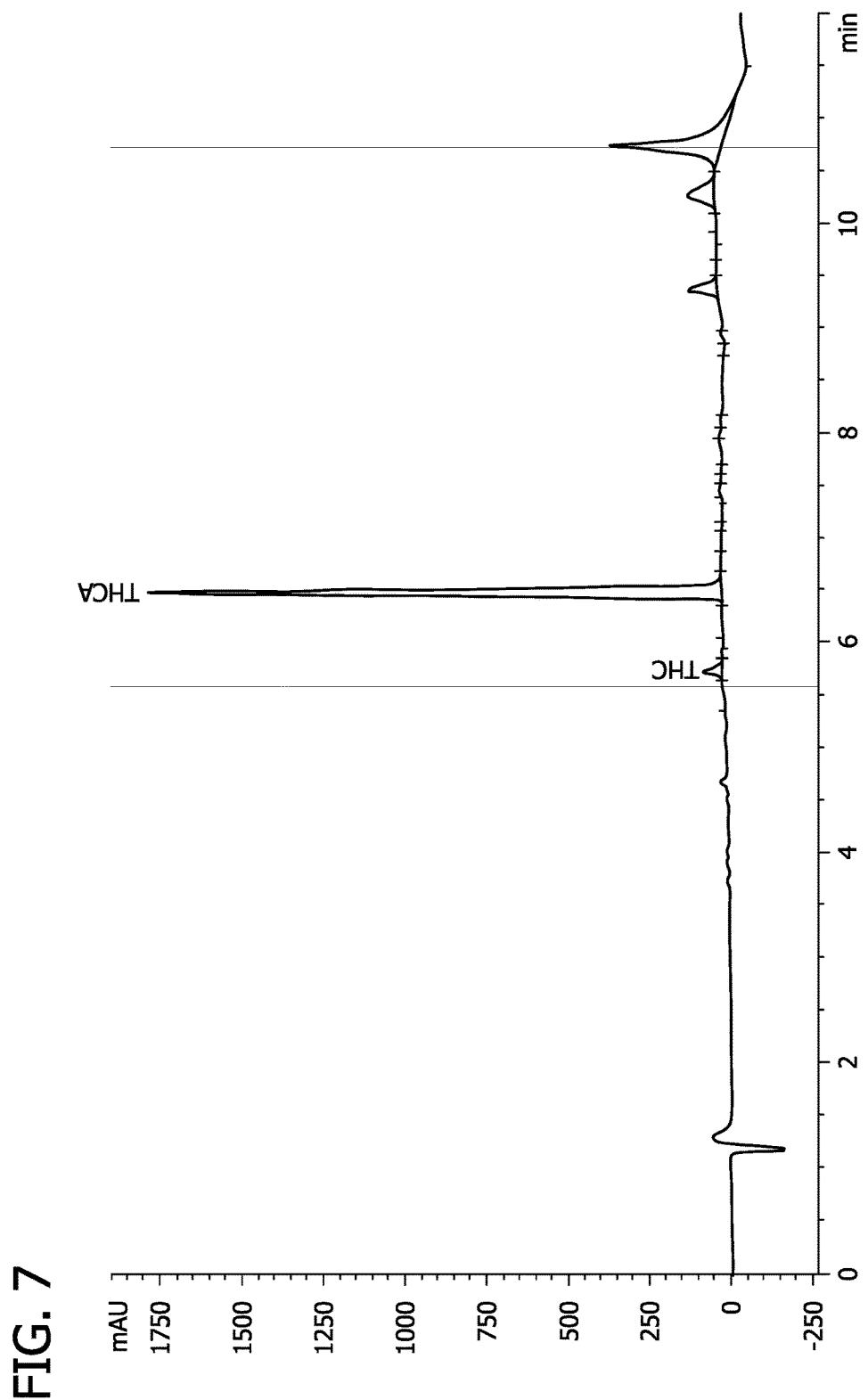
FIG. 7 shows the chromatography analysis of the THCA rich solution of FIG. 6 after processing.

FIG. 6 shows the chromatography analysis, at 220 nm, of a THCA rich cannabinoid-containing extract feed before being treated with an adsorbent. An adsorbent having a weight ratio of 2:1:1 of silica:charcoal:FLORISIL was used to prepare a pre-treated extract. The silica used is SiliCycle UltraPure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. The pre-treated extract stream was then contacted with a whatman #1 filter paper having a pore size of 11 μm, to remove the residual adsorbent. The pre-treated extract was finally contacted with a SolSep NF090801 filter (350 dalton MWCO), in a dead end cell configuration, at a pressure of 250 psi and a temperature of 25° C. The analysis of the retentate of this filtration can be seen in FIG. 7.

The increased peak height of the THCA demonstrates that a higher concentration of THCA was achieved relative to the pre-treated extract stream.

Example 6: Treatment of a CBDA Rich Stream

Figure 8:
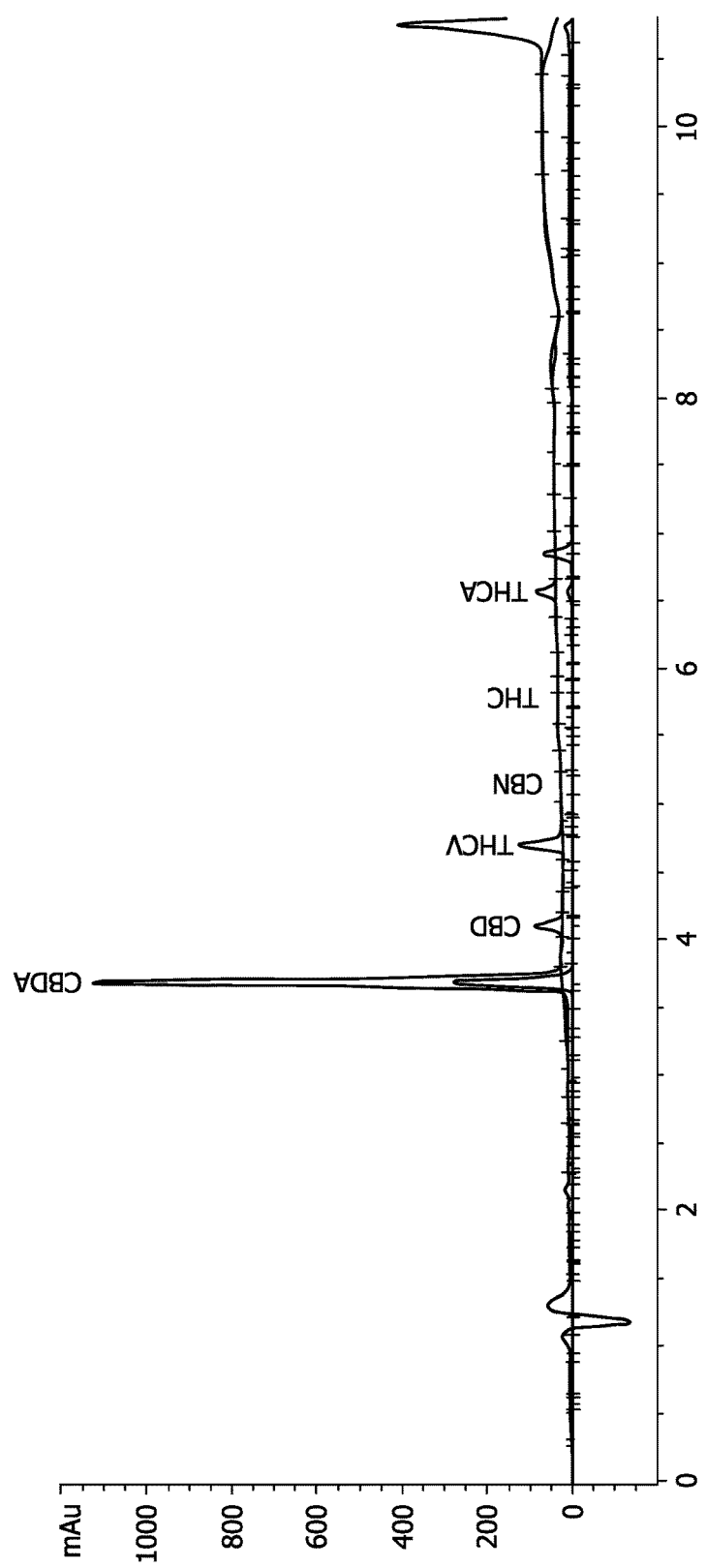
FIG. 8 shows the chromatography analysis of a concentrated cannabinoid product produced from a CBDA rich pre-treated extract stream which was subjected to filtration and recovered using an extractant.

A CBDA rich cannabinoid-containing extract feed was treated with an adsorbent having a weight ratio of 2:1:1 of silica:charcoal:FLORISIL. The silica used was SiliCycle UltraPure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. The pre-treated extract stream was then contacted with a whatman #1 filter paper having a pore size of 11 μm, to remove the residual adsorbent. The pre-treated extract was contacted with a SolSep NF090810 filter (350 dalton MWCO), in a dead end cell configuration, at a pressure of 250 psi, and at a temperature of 25° C. to obtain a concentrated cannabinoid product in the permeate stream. The permeate was contacted with MCT oil, as an extractant, and a concentrated cannabinoid-containing product was obtained. FIG. 8 shows the chromatography analysis, at 220 nm, of the concentrated cannabinoid product produced from the CBDA rich cannabinoid-containing extract feed.

Figure 9:
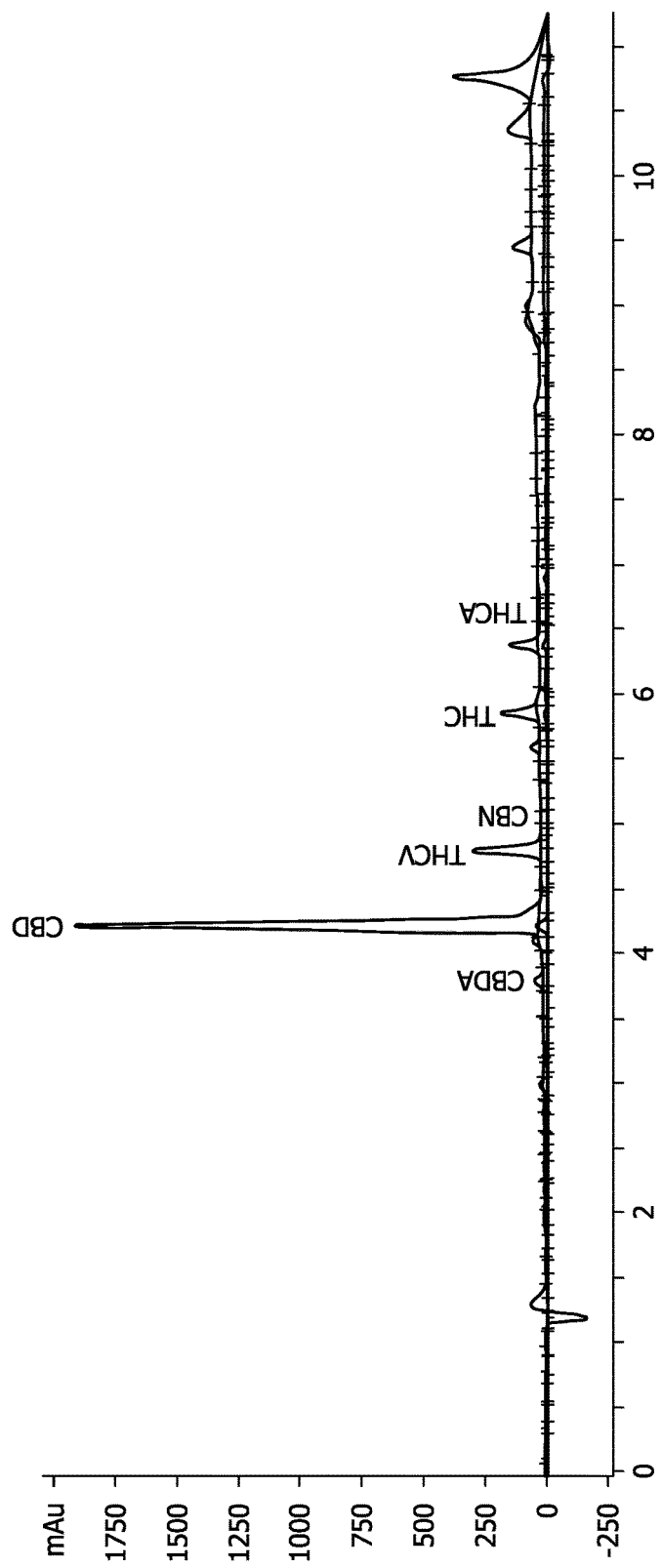
FIG. 9 shows the chromatography analysis of the concentrated cannabinoid product of FIG. 8 after the product was subjected to decarboxylation.

FIG. 9 shows the chromatography analysis, at 220 nm, of the concentrated cannabinoid product of FIG. 8 after the product was subjected to decarboxylation by heating the product to 75° C. in a closed vessel.

Example 7: Treatment of a THCA Rich Stream

Figure 10:
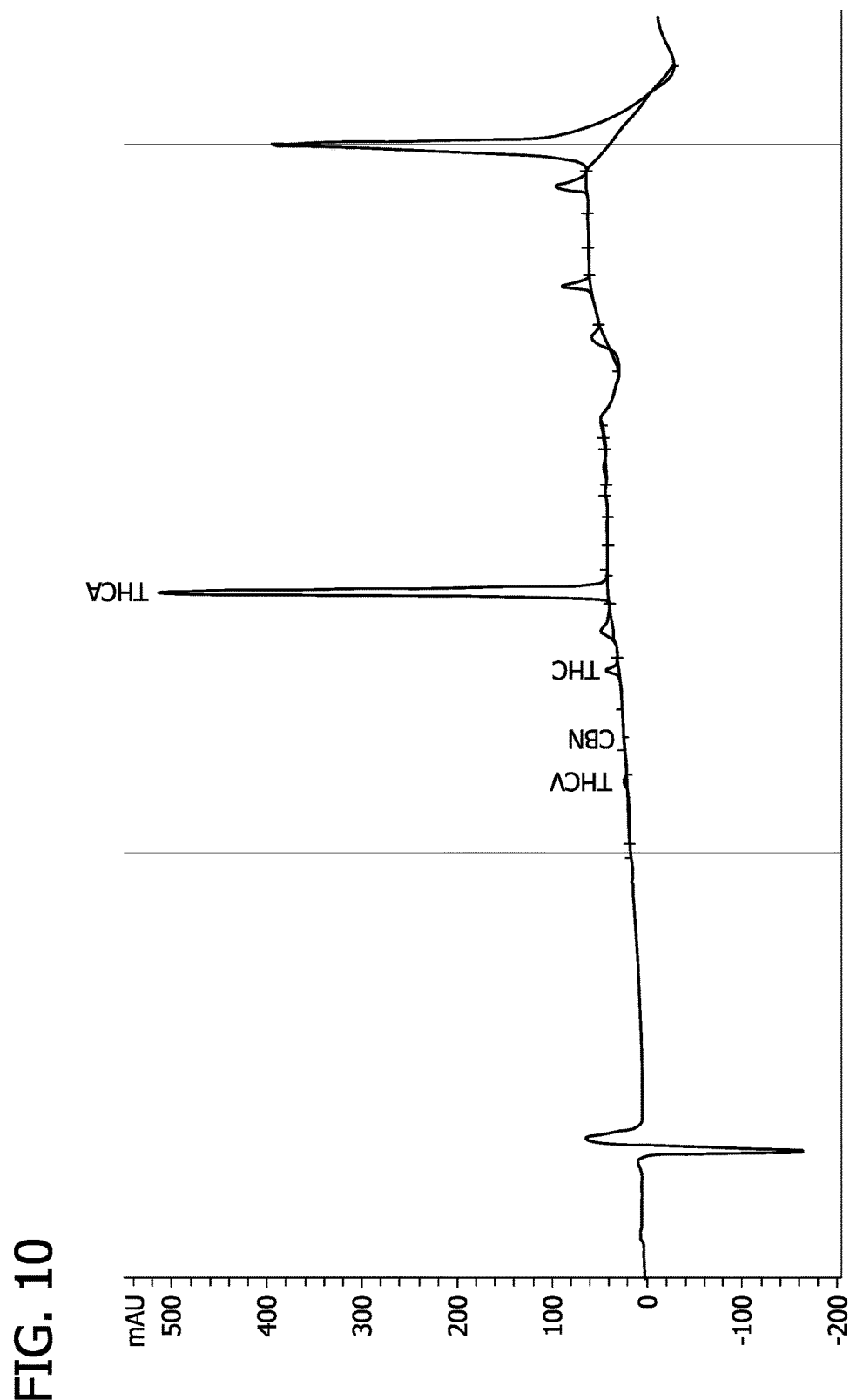
FIG. 10 shows the chromatography analysis of a concentrated cannabinoid product produced from a THCA rich pre-treated extract stream which was subjected to filtration and recovered using an extractant.

A THCA rich cannabinoid-containing extract feed was contacted with an adsorbent and filter paper as in Example 6. The pre-treated extract was then contacted via tangential flow with a 1,100 dalton MWCO ceramic filter comprising 19 channel ceramic elements on α-alumina support, comprising $TiO_2$ layers with $TiO_2ZrO_2$ composite. The permeate was contacted with MCT oil, as an extractant, and a concentrated cannabinoid-containing product was obtained. FIG. 10 shows the size exclusion chromatography analysis of the concentrated cannabinoid product produced from the THCA rich cannabinoid-containing extract feed.

Figure 11:
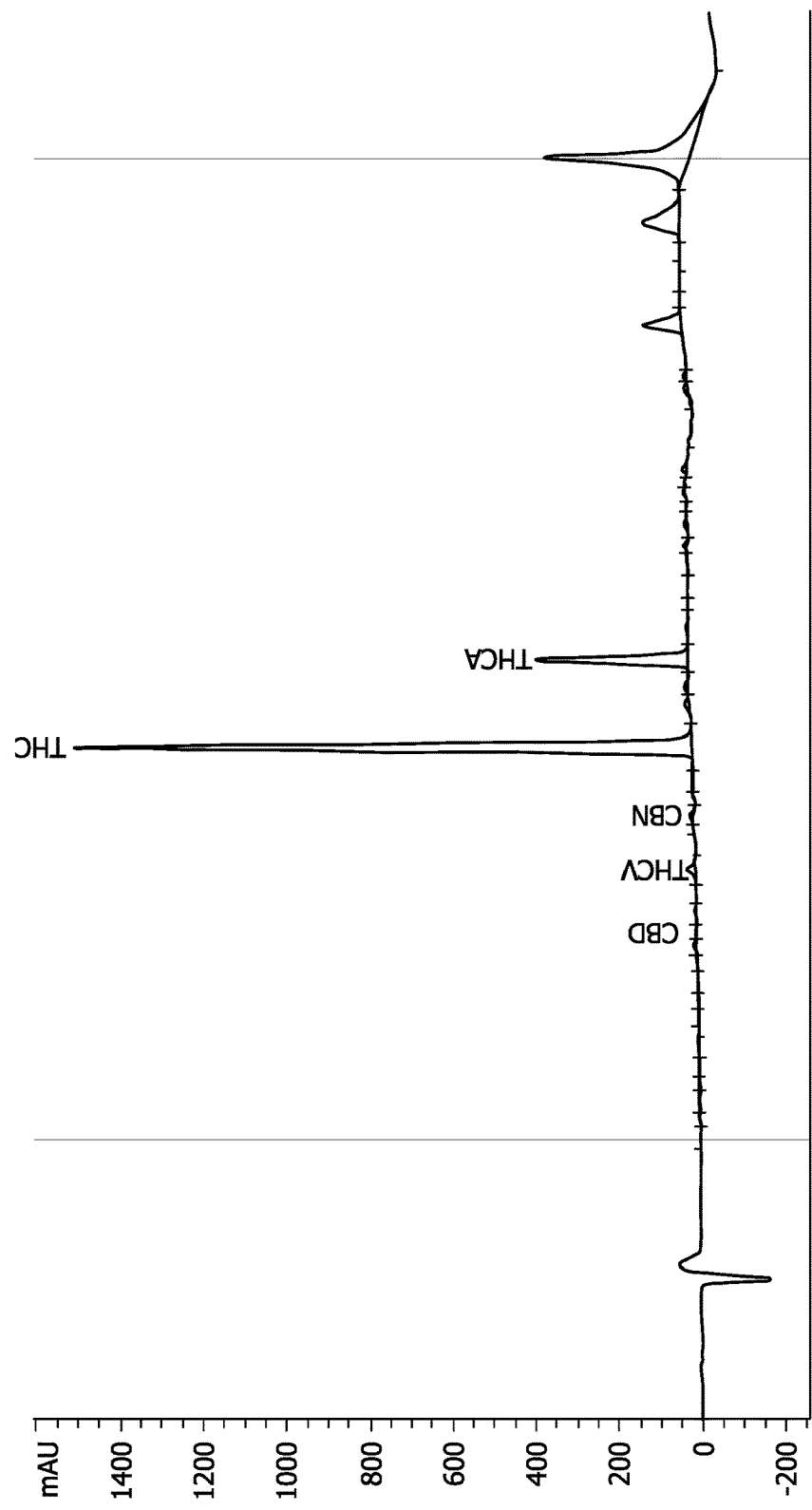
FIG. 11 shows the chromatography analysis of the concentrated cannabinoid product of FIG. 10 after the product was subjected to decarboxylation.

FIG. 11 shows the size exclusion chromatography analysis of the concentrated cannabinoid product of FIG. 10 after the product was subjected to decarboxylation by heating the product to 75° C. in a closed vessel.

Example 8: Terpene Analysis

Figure 12:
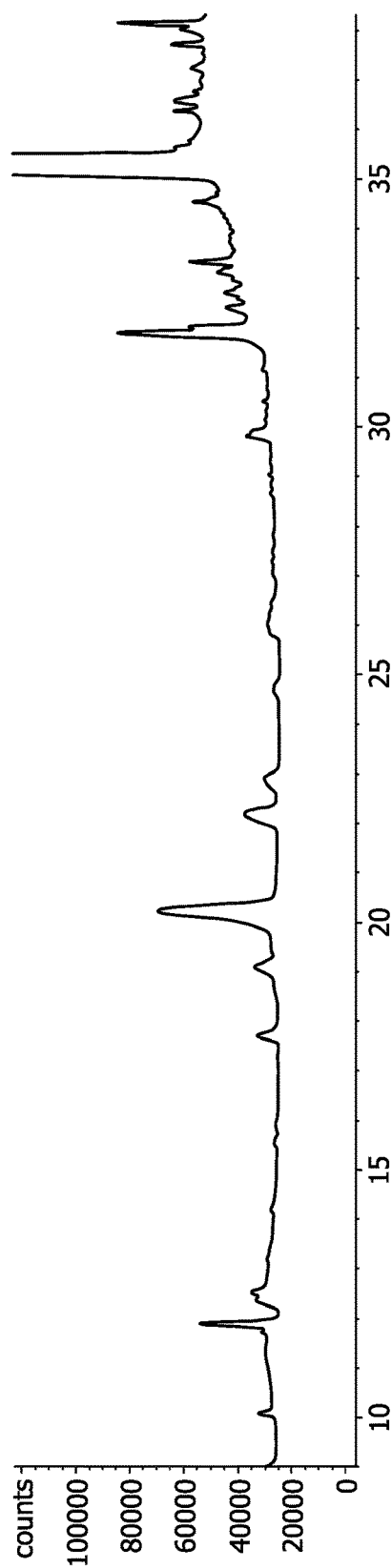
FIG. 12 shows the gas chromatography analysis of the terpene content observed in a cannabinoid-containing extract feed comprising ethanol.
Figure 13:
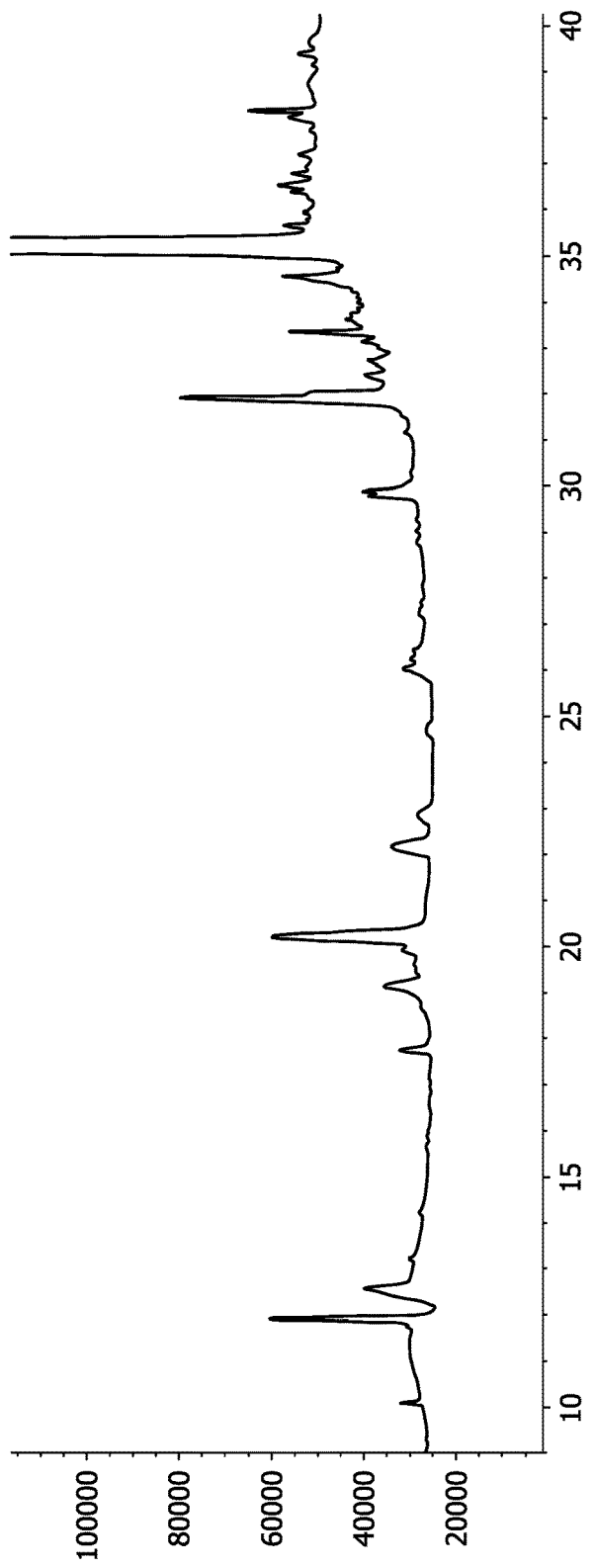
FIG. 13 shows the terpene content of the solution of FIG. 12 after treatment with silica, charcoal, and FLORISIL.
Figure 14:
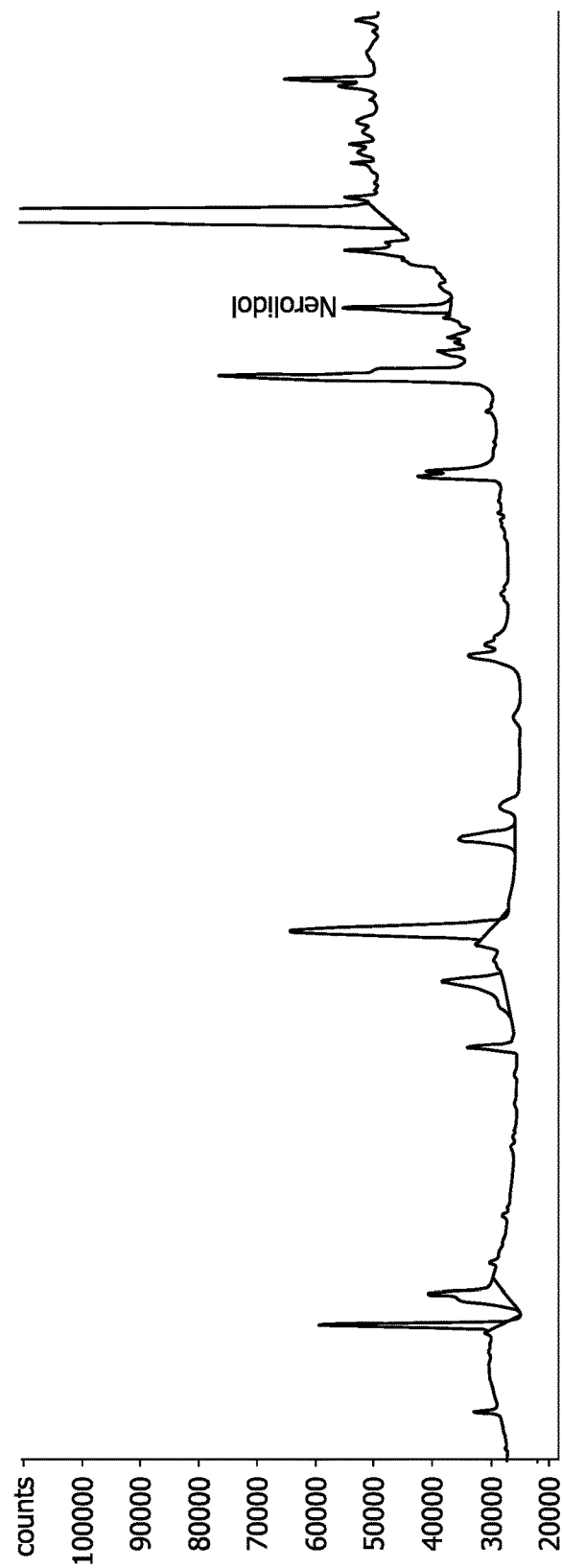
FIG. 14 shows the terpene content of the solution of FIG. 13 after filtration.
Figure 15:
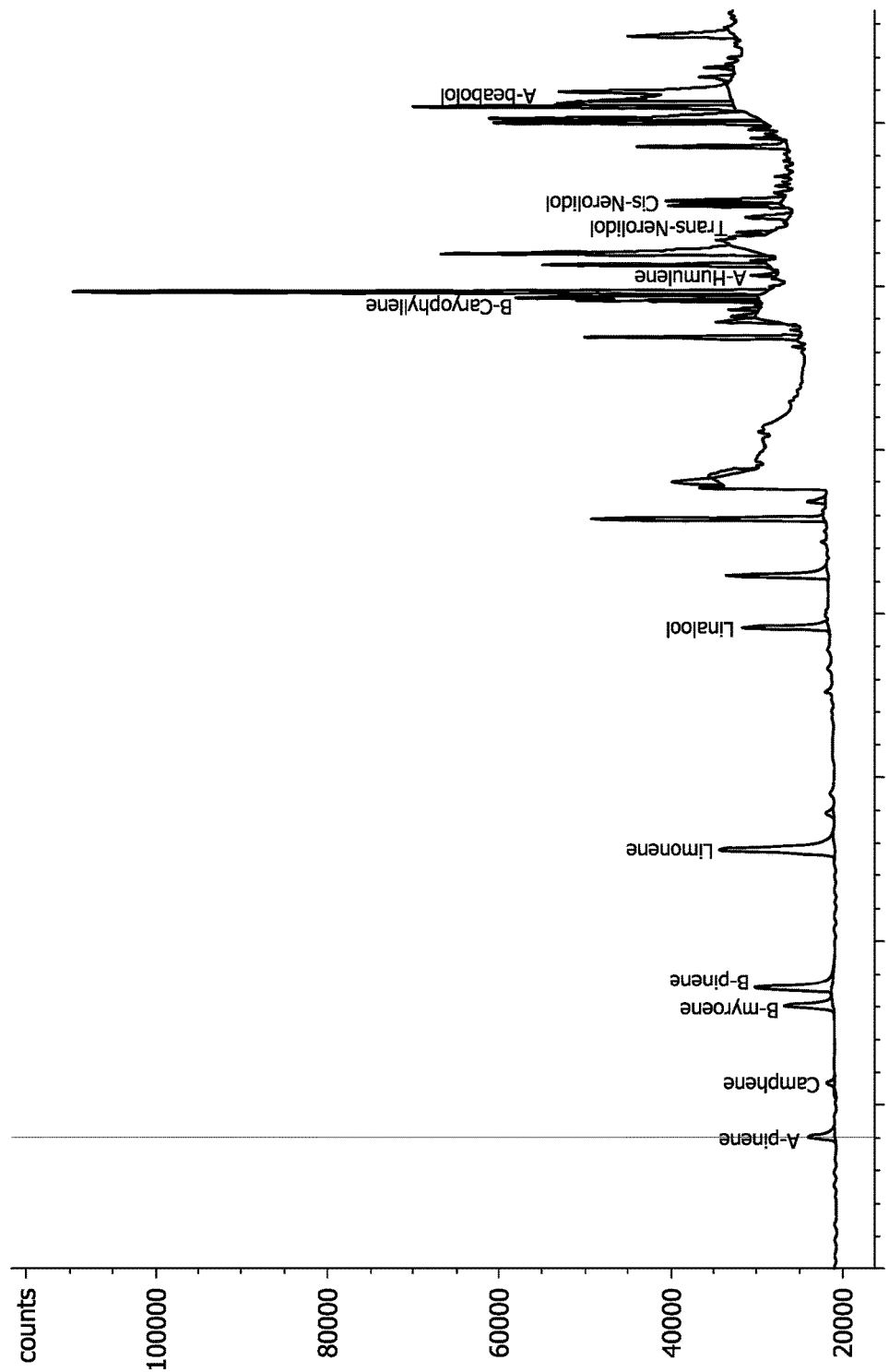
FIG. 15 shows the terpene content following recovery of a concentrated cannabinoid product from the solution of FIG. 14.
Figure 16:
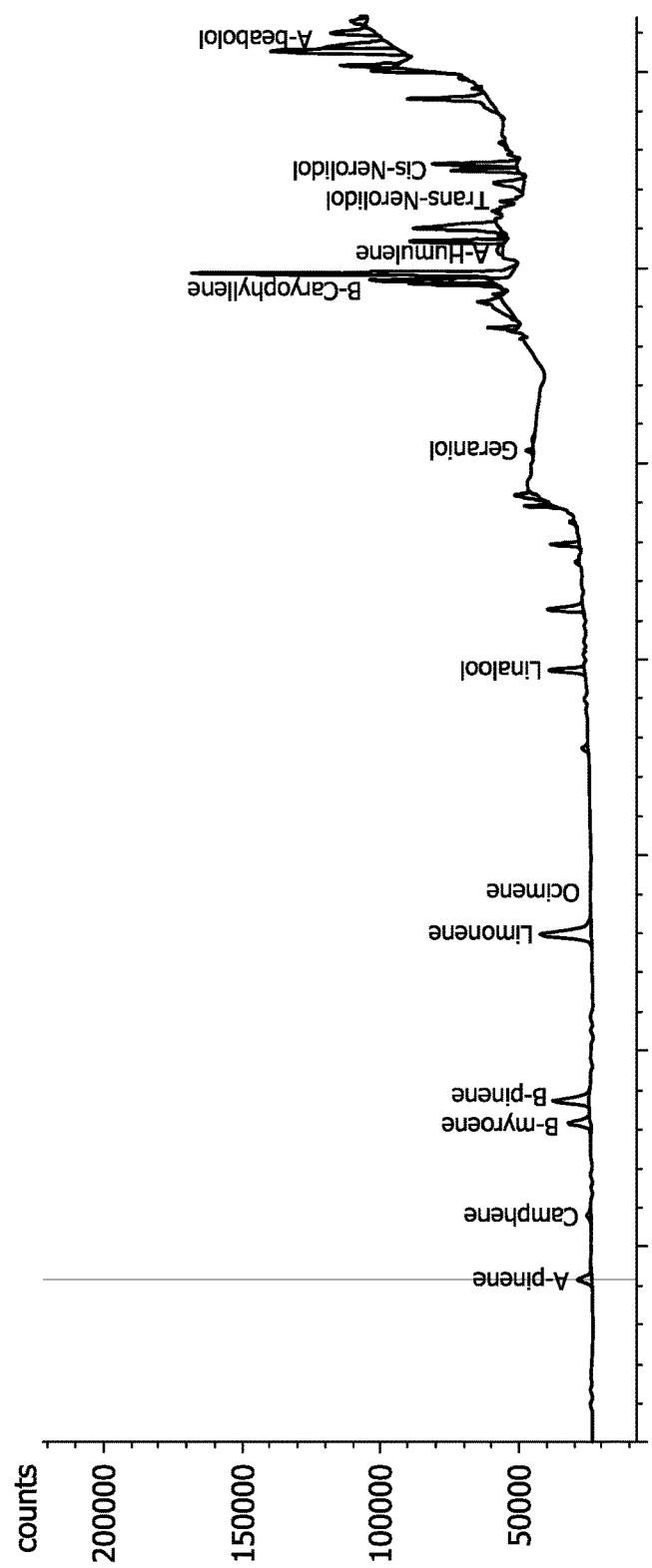
FIG. 16 shows the terpene content of the concentrated product of FIG. 15 after the product has been decarboxylated.

FIG. 12 shows the gas chromatography analysis, using flame ionization detection (FID), of the terpene content observed in a cannabinoid-containing extract feed comprising ethanol. FIG. 13 then shows the terpene content of the pre-treated extract prepared by subjecting the cannabinoid-containing extract feed of FIG. 12 to an adsorbent having a weight ratio of 2:1:2 of silica:charcoal:FLORISIL. The silica used was SiliCycle UltraPure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. Next, FIG. 14 shows the terpene content of the second retentate following extract filtration. The extract filtration comprised contacting the pre-treated extract with a SolSep NF08105 filter (1000 dalton MWCO), in a dead end cell configuration, and then contacting the first permeate with a SolSep NF090801 filter (350 dalton MWCO), in a dead end cell configuration. Both filter operations were performed at a pressure of 250 psi and a temperature of 25° C. FIG. 15 shows the terpene content of the final concentrated cannabinoid product. Finally, FIG. 16 shows the terpene content of the concentrated cannabinoid product of FIG. 15 after the product was decarboxylated by heating the product to 75° C. in a closed vessel.

It was observed that there was no significant decrease in terpene content throughout the process. In fact, the terpene peaks were more clearly defined as each step of the process proceeded. The only observable loss in terpenes occurred after the final product was subjected to decarboxylation. It is believed that subsequent testing may reduce the terpene loss by modifying the heat and pressure of this decarboxylation operation.

On average, a terpene content of 0.4-0.5 mg/ml is observed throughout the process. However, one skilled in the art will understand that the terpene content will depend to a certain extent on the amount of terpenes present in the starting material.

Example 9: Flavonoid Analysis

Figure 17:
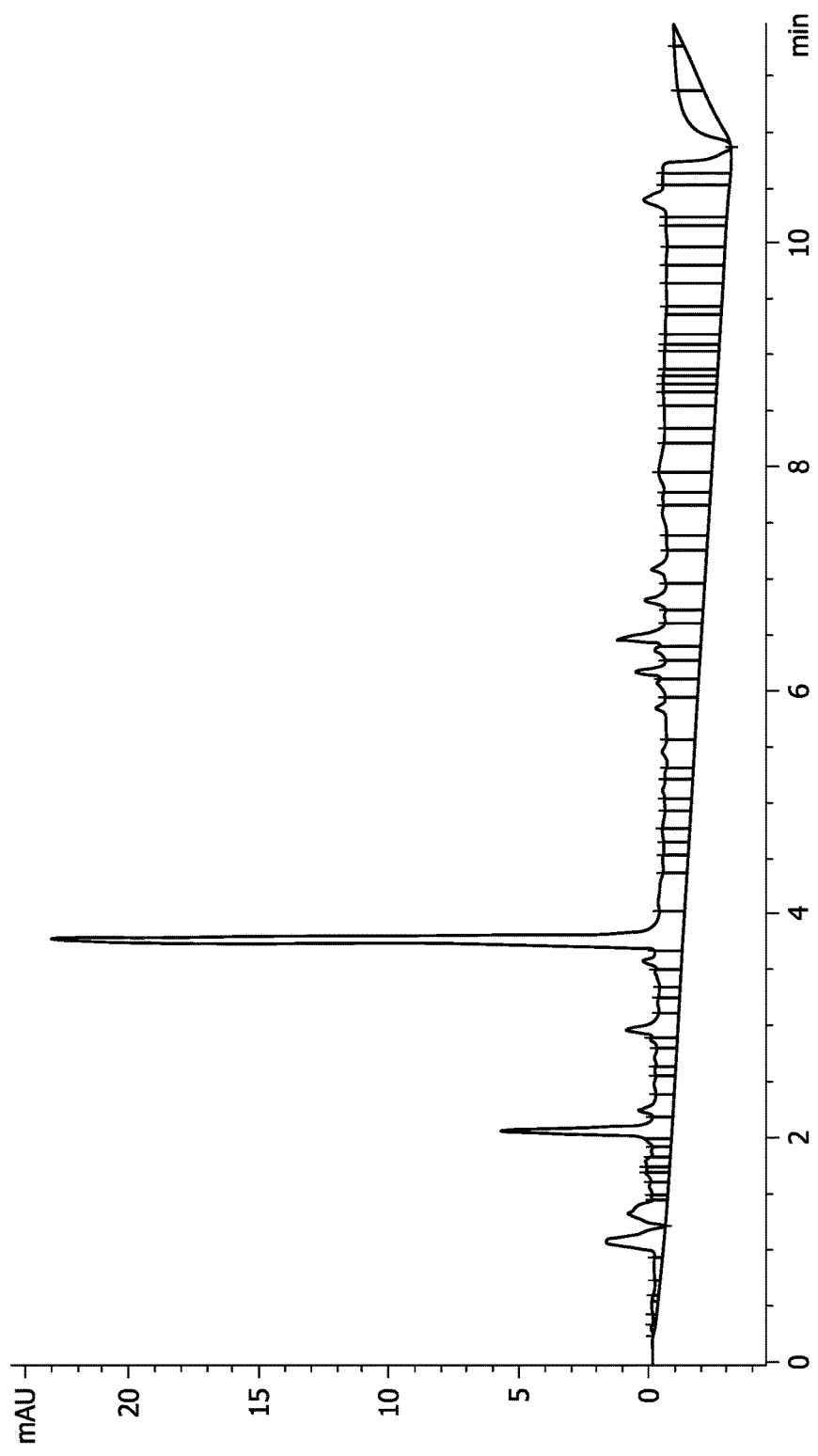
FIG. 17 shows the liquid chromatography of the flavonoid content of a cannabinoid-containing extract feed comprising ethanol.
Figure 18:
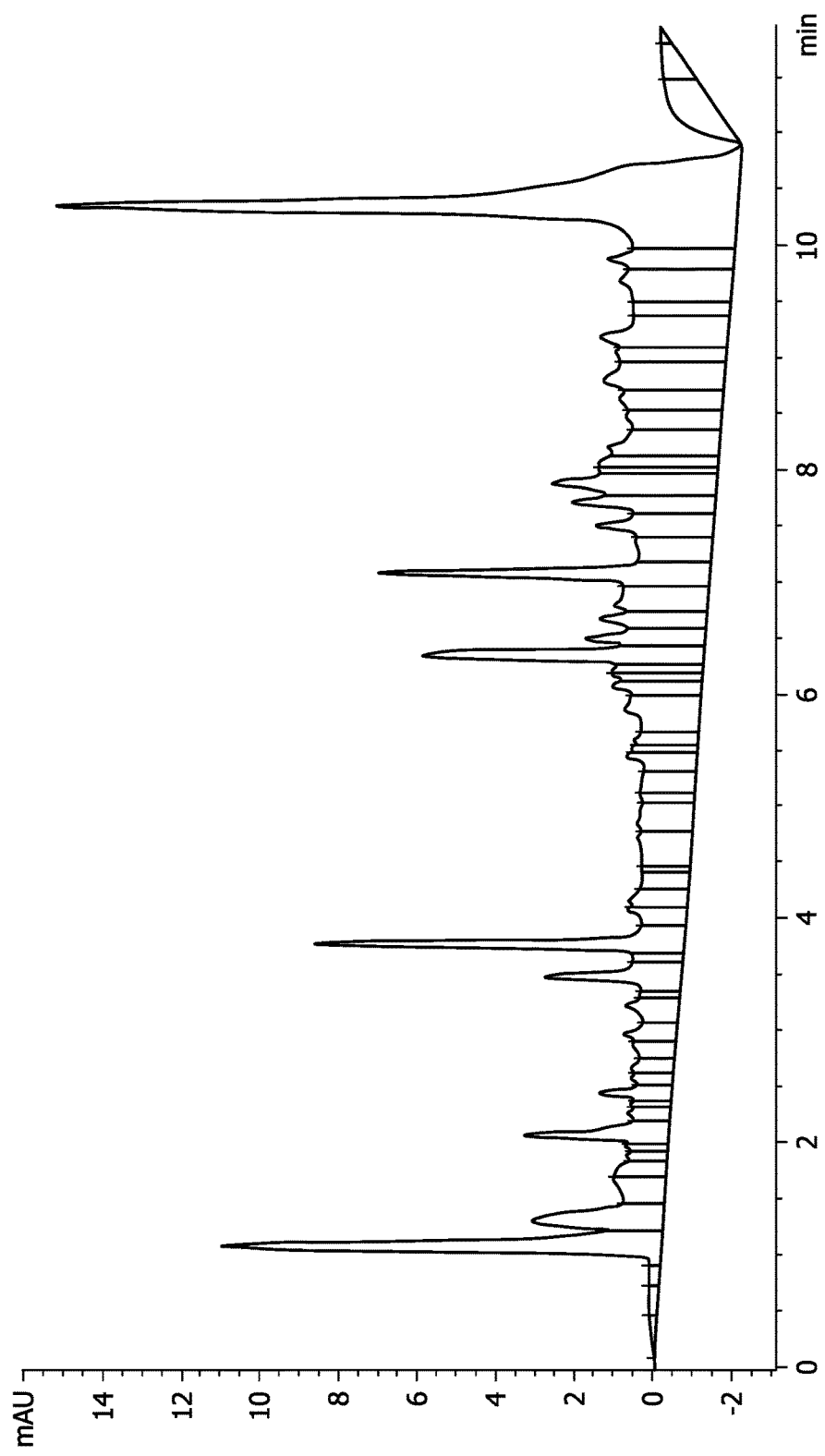
FIG. 18 shows the flavonoid content of the pre-treated extract prepared by subjecting the cannabinoid-containing extract feed to silica, charcoal, and FLORISIL.
Figure 19:
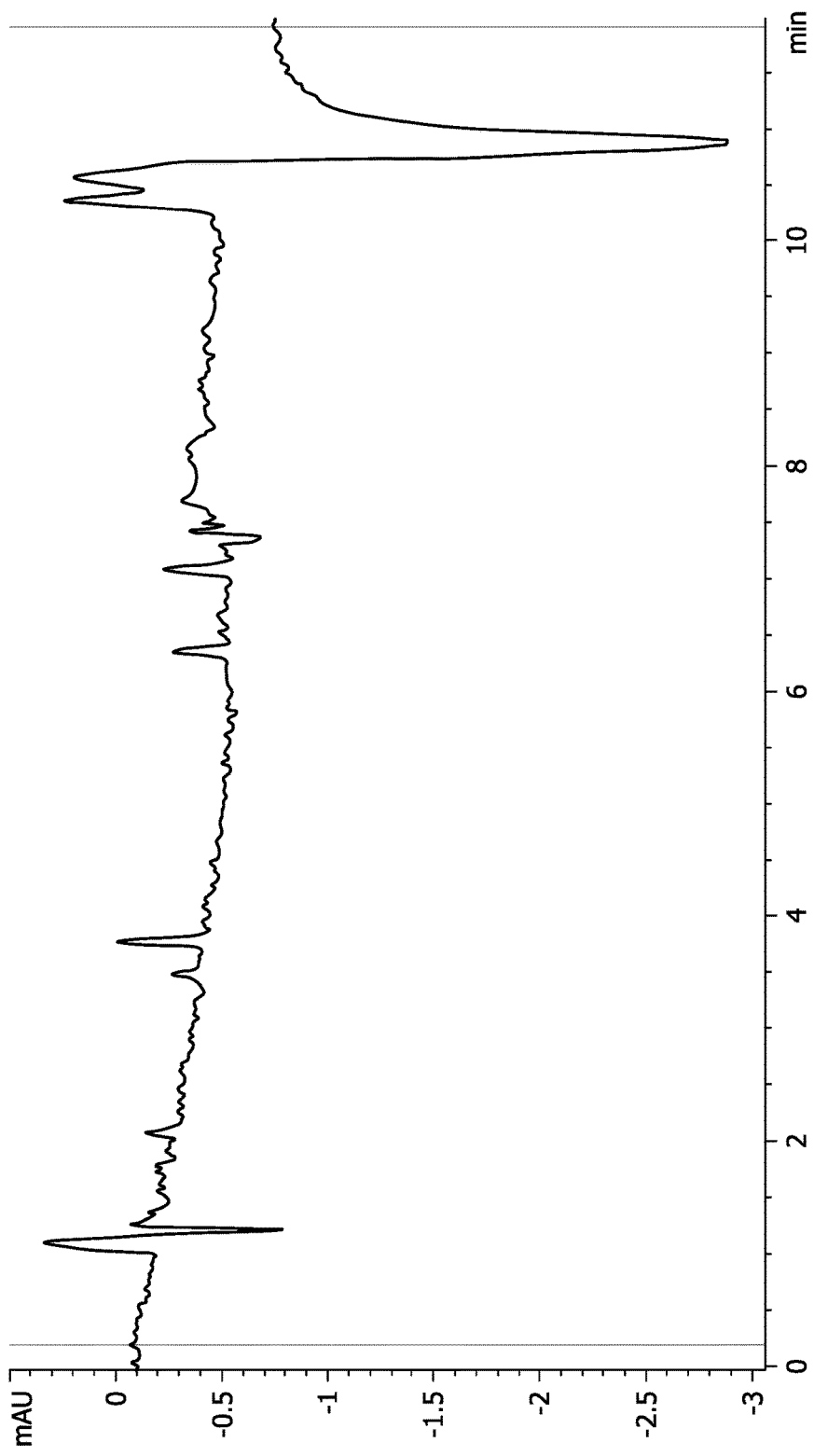
FIG. 19 shows the liquid chromatography results of flavonoid content of the solution of FIG. 18, diluted by a factor of twenty.
Figure 20:
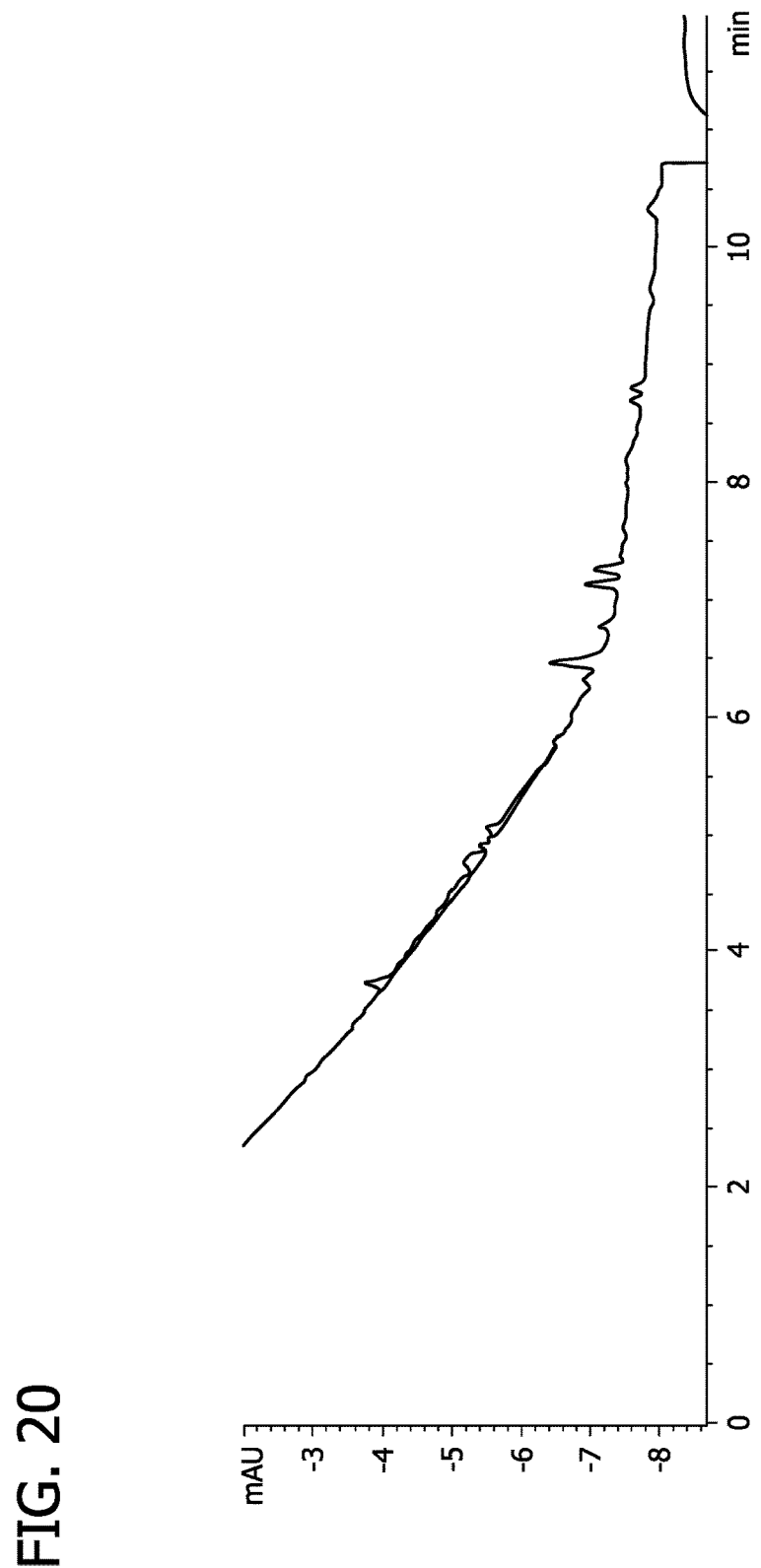
FIG. 20 shows the flavonoid content of the solution of FIG. 19 after subjected to extract filtration and contacted with the extractant MCT oil.

FIG. 17 shows the liquid chromatography analysis, at 370 nm, of the flavonoid content of a cannabinoid-containing extract feed comprising ethanol. FIG. 18 shows the flavonoid content of the pre-treated extract prepared by subjecting the cannabinoid-containing extract feed to an adsorbent having a weight ratio of 2:1:2 of silica:charcoal:FLORISIL. The silica used was SiliCycle UltraPure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. The pre-treated extract was then diluted by a factor of twenty and analyzed via liquid chromatography, at 370 nm, as seen in FIG. 19. The diluted pre-treated extract was contacted with a SolSep NF08105 filter (1000 dalton MWCO), in a dead end cell configuration, and then the first permeate was contacted with a SolSep NF090801 filter (350 dalton MWCO), in a dead end cell configuration. Both filter operations were performed at a pressure of 250 psi and a temperature of 25° C. Finally, the second retentate was contacted with MCT oil, as an extractant, and a concentrated cannabinoid-containing product was obtained. FIG. 20 shows the flavonoid content of the concentrated cannabinoid-containing product.

Noting that the scale of FIG. 18 is almost half the value of the scale of FIG. 17, flavonoids are observed to be highly susceptible to removal from the process when treated with silica, charcoal, and FLORISIL. While a reduction of about 50% of flavonoids may be observed by treatment with silica, charcoal, and FLORISIL, prolonged exposure may greatly reduce the flavonoid content, for example to about 0%. It is further observed that reduction in flavonoid content during extract filtration and recovery of the concentrated cannabinoid product are minimal when compared to the high observed reduction during production of a pre-treated extract.

Flavonoid peaks observed around UV (370 nm) may be of biological significance. Therefore, in certain embodiments it may be desirable to treat the cannabinoid-containing extract for such a time as to maximize flavonoid content.

Example 10: Cannabinoid and Terpene Content During Process

Figure 21:
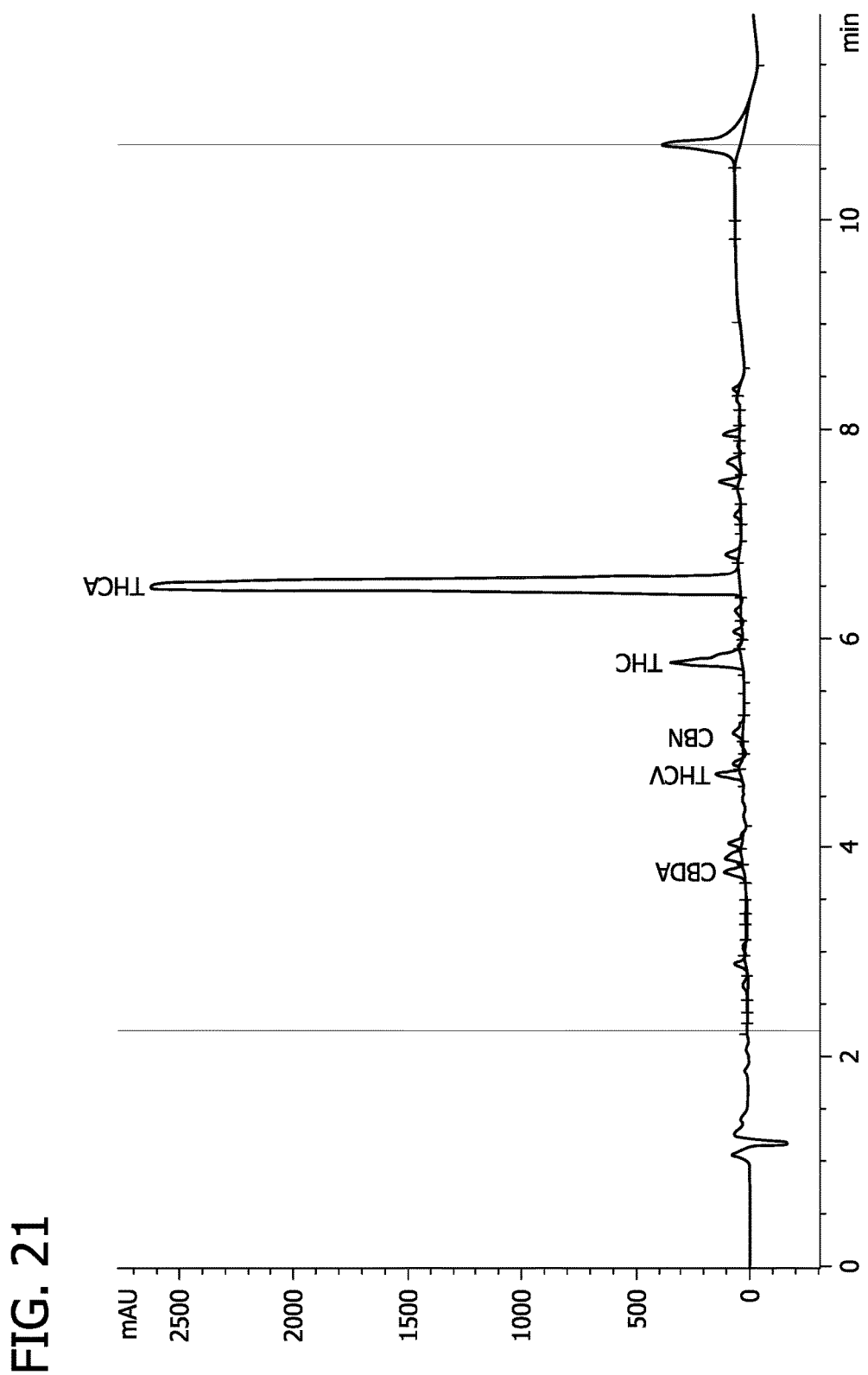
FIG. 21 shows the chromatography analysis of the initial cannabinoid content of a cannabinoid-containing extract feed at 220 nm.
Figure 22:
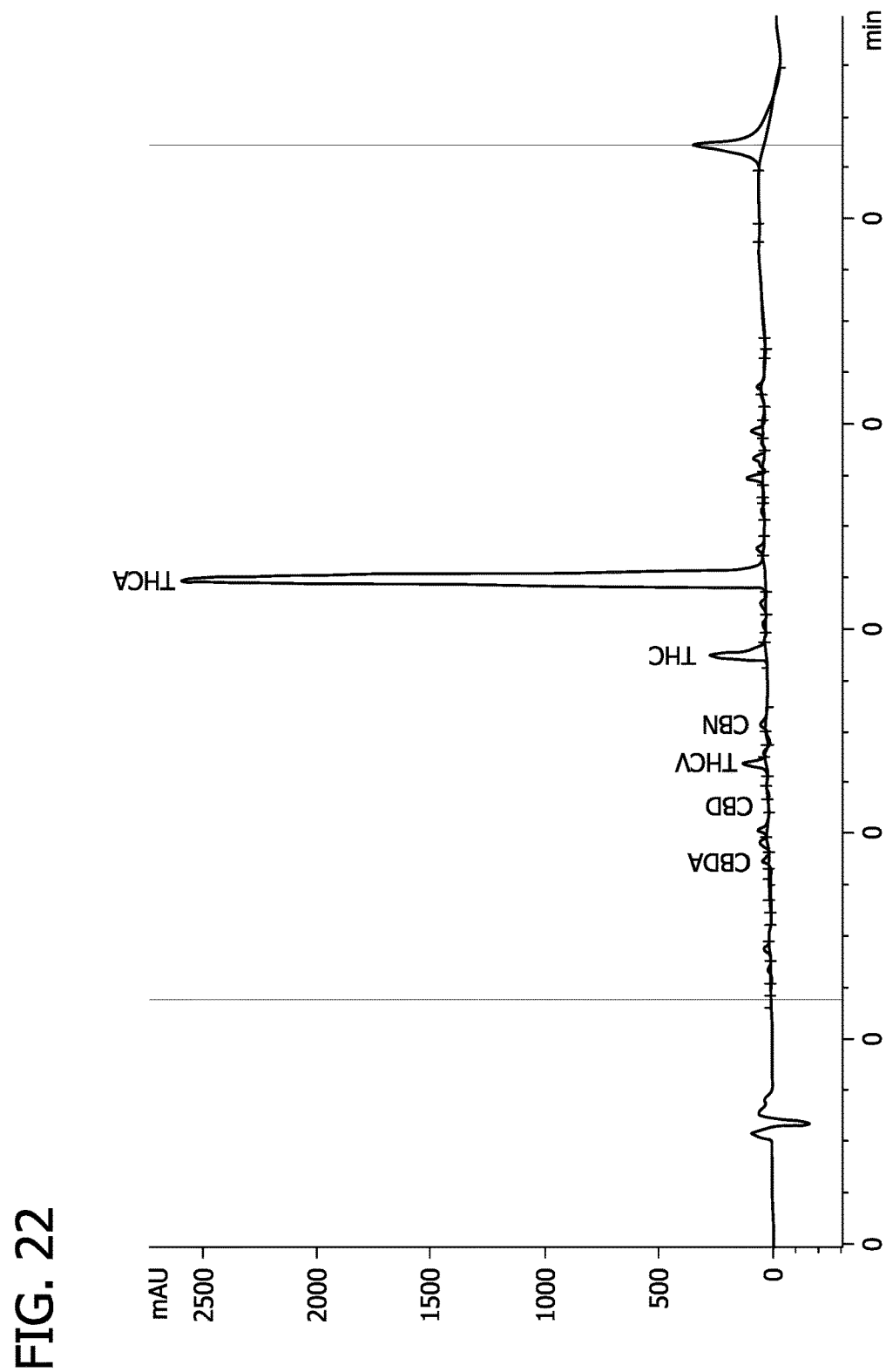
FIG. 22 shows the cannabinoid content of the first permeate of the stream of FIG. 21.
Figure 23:
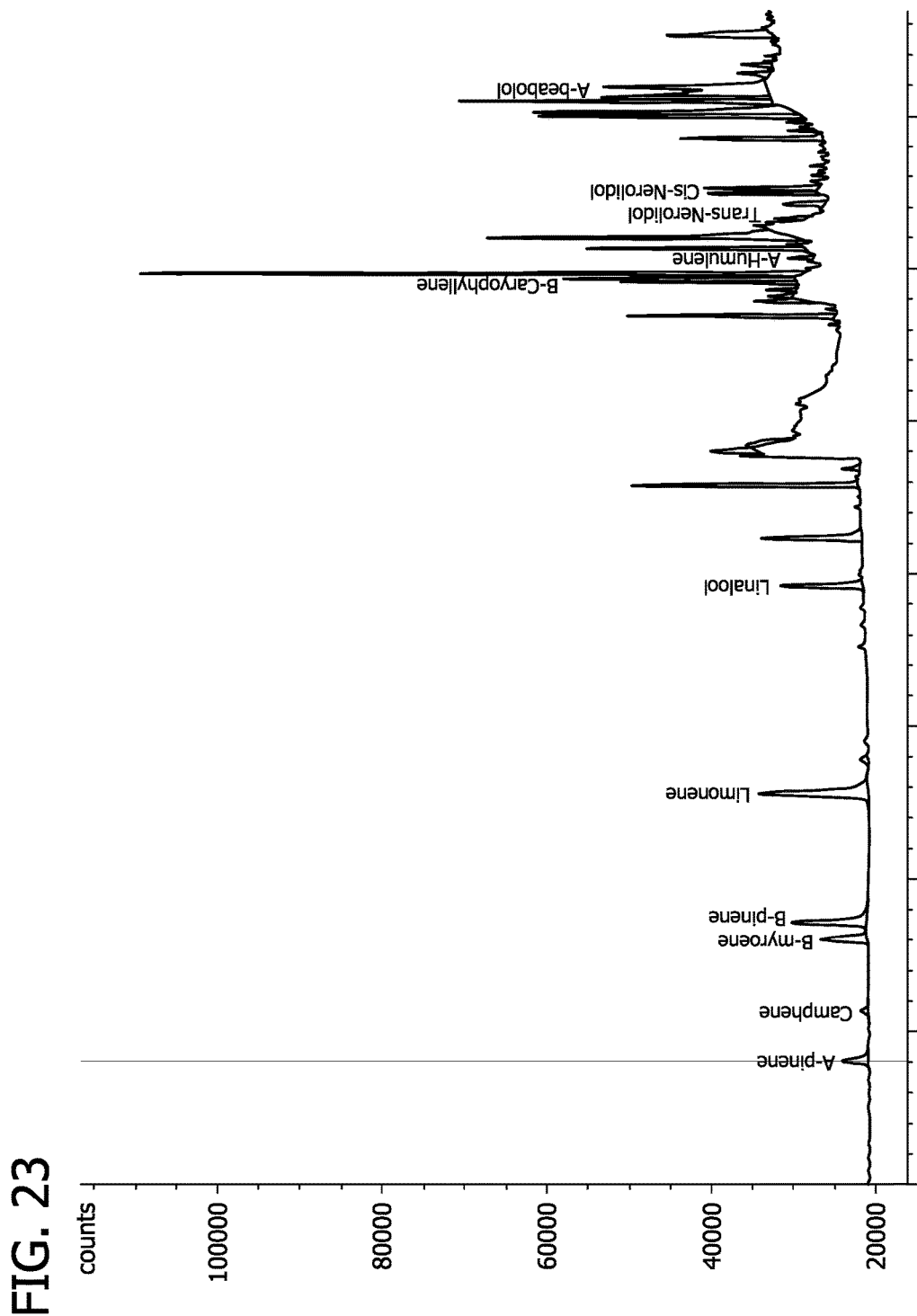
FIG. 23 shows the terpene content of the first permeate of the stream of FIG. 21.

FIG. 21 shows the chromatography analysis of the initial cannabinoid content of a cannabinoid-containing extract feed at 220 nm. A pre-treated extract was prepared by subjecting the cannabinoid-containing extract feed to an adsorbent having a weight ratio of 2:1:2 of silica:charcoal:FLORISIL. The silica used was SiliCycle UltraPure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. The pre-treated extract stream was then contacted with a whatman #1 filter paper having a pore size of 11 µm, to remove the residual adsorbent. The pre-treated extract feed was then contacted with a SolSep NF08105 filter (1000 dalton MWCO), in a dead end cell configuration, at a pressure of 250 psi, and at a temperature of 25° C. FIG. 22 shows the cannabinoid content of the first permeate while FIG. 23 shows the terpene content of the first permeate.

Figure 24:
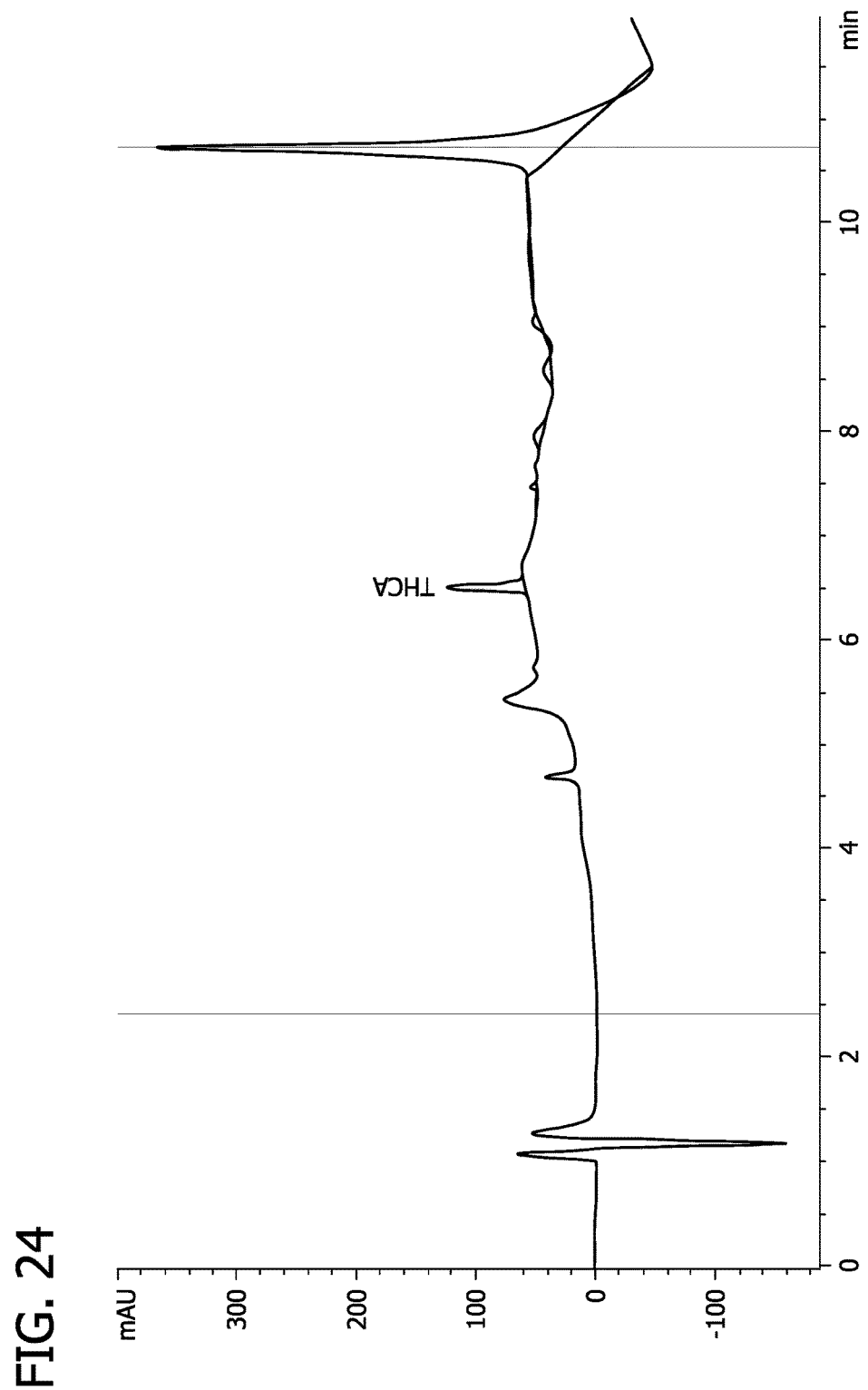
FIG. 24 shows the cannabinoid content of the second permeate of the stream of FIG. 21.
Figure 25:
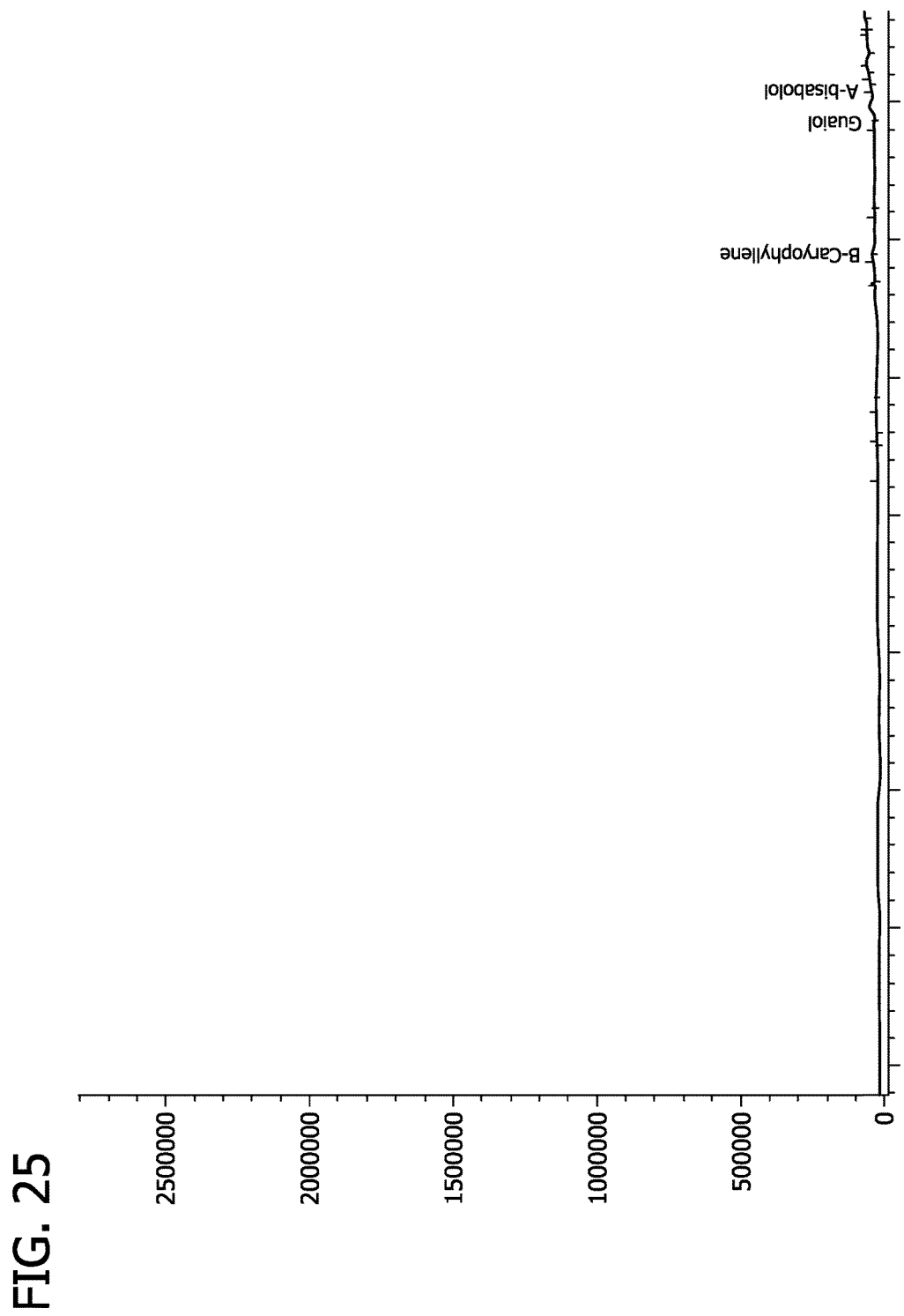
FIG. 25 shows the terpene content of the second permeate of the stream of FIG. 21.
Figure 26:
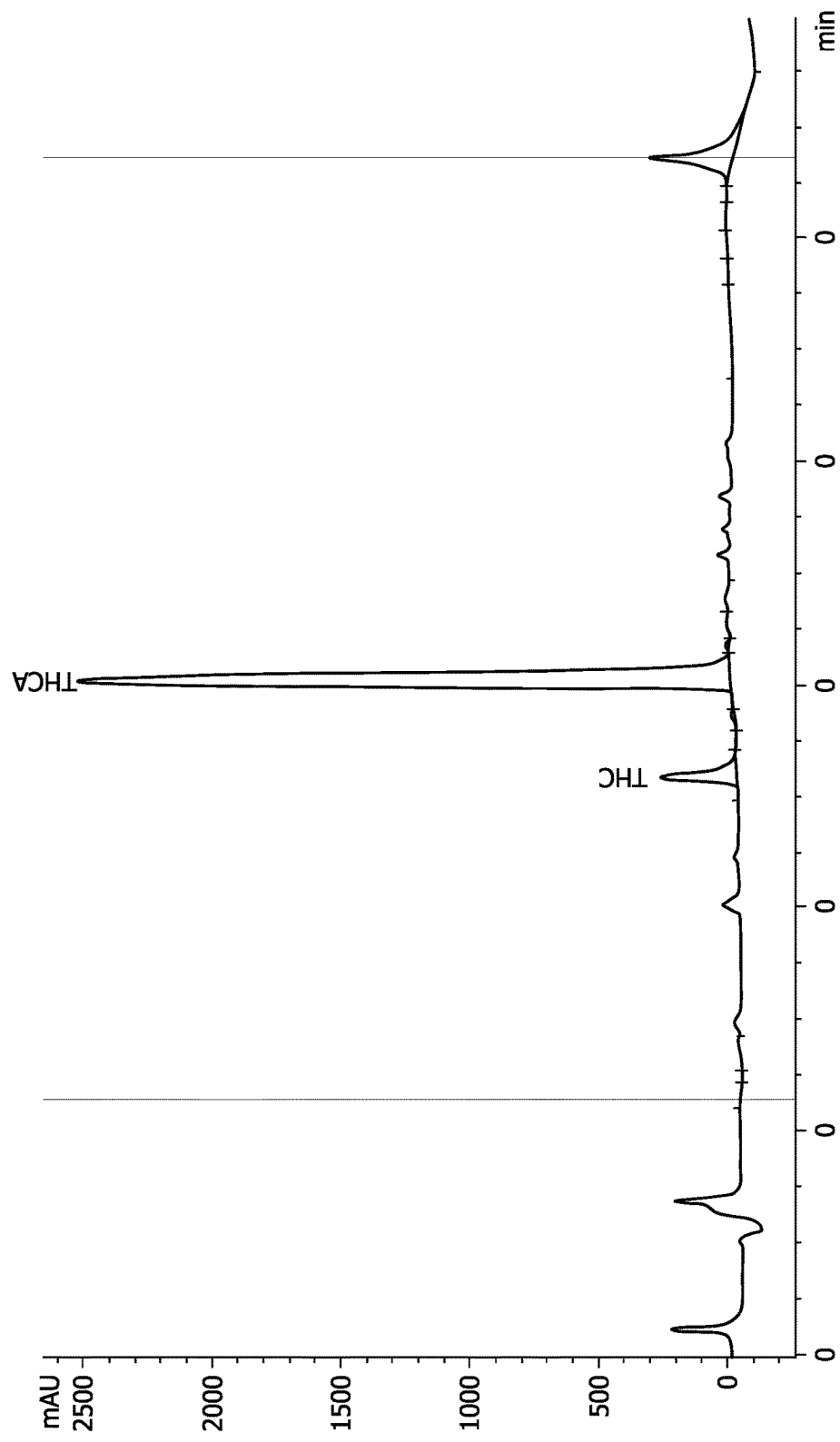
FIG. 26 shows the concentration of cannabinoids in the second retentate of the stream of FIG. 21.

The first permeate was then contacted with a SolSep NF090801 filter (350 dalton MWCO) at a pressure of 250 psi and a temperature of 25° C. A second permeate was generated at a rate of 0.02 mg/ml. FIG. 24 shows the cannabinoid content of the second permeate while FIG. 25 shows the terpene content of the second permeate. It can be observed that there was a very small amount of terpenes present in the second permeate, indicating that the majority of the terpenes were located in the second retentate. The second retentate was generated at a rate of 4.0 mg/ml and the concentration of cannabinoids in the second retentate can be seen in FIG. 26.

Example 11: Experimental vs. Theoretical Purities

A THC-rich cannabinoid-containing extract feed and a CBD-rich cannabinoid-containing extract feed were each independently processed.

The cannabinoid-containing extract feed was treated with an adsorbent having a weight ratio of 2:1:1 of silica:charcoal:FLORISIL. The silica used was SiliCycle Ultra-Pure (approximate particle size 40 mesh). The charcoal used was decolorizing activated charcoal obtained from Sigma-Aldrich Co. (approximate particle size 100 mesh). The FLORISIL obtained from Sigma-Aldrich Co. had a particle size of approximately 100 mesh. The pre-treated extract stream was then contacted with a whatman #1 filter paper having a pore size of 11 µm, to remove the residual adsorbent. The pre-treated extract was contacted with a SolSep NF08105 filter (1000 dalton MWCO), in a dead end cell configuration, at a pressure of 250 psi, and at a temperature of 25° C. The first permeate of this extraction was then contacted with a SolSep NF090801 filter (350 dalton MWCO), in a dead end cell configuration, at a pressure of 250 psi, and at a temperature of 25° C. Next, the second retentate was contacted with MCT oil, as an extractant, to produce a concentrated cannabinoid-containing product. The concentrated cannabinoid-containing product was diluted by a factor of 20 and analyzed via HPLC assay.

The THC content of the processed THC-rich cannabinoid-containing extract feed can be seen below in Table 1. The CBD content of the processed CBD-rich cannabinoid-containing extract feed can be seen below in Table 2. In each instance, "Expected" THC or CBD content corresponds to the total theoretically available THC/CBD content in the starting cannabinoid-containing extract feed. It can be seen that a low proportion of the desired cannabinoid is lost during processing. Therefore, a concentrated cannabinoid containing product can be made while retaining the majority of the theoretically available cannabinoids present in the starting material.

TABLE 1

| Extraction 1 THC (g) | |
| --- | --- |
| Expected | 7.1 |
| Observed | 6.6 |
| Yield | 92.9% |

TABLE 2

| Extraction 2 CBD (g) | |
| --- | --- |
| Expected | 6.4 |
| Observed | 6.15 |
| Yield | 96.0% |

When introducing elements of the present invention or the preferred embodiments(s) thereof, the articles "a", "an", "the" and "said" are intended to mean that there are one or more of the elements. The terms "comprising", "including" and "having" are intended to mean that there may be additional elements other than the listed elements.

In view of the above, it will be seen that the several objects of the invention are achieved and other advantageous results attained.

As various changes could be made in the above processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

What is claimed is:

1. A process for preparing a concentrated cannabinoid product, comprising
    contacting a cannabinoid-containing extract feed comprising cannabinoids and a solvent with a solid adsorbent to adsorb large molecule impurities from the cannabinoid-containing extract feed and produce a pre-treated extract;
    contacting the pre-treated extract with a first filter having a 400-5,000 dalton MWCO (molecular weight cut-off) to produce a first retentate comprising large molecular weight impurities and a first permeate comprising cannabinoids;
    combining the first permeate and a liquid phase extractant to form a filtrate extraction mixture comprising an extract phase comprising cannabinoids and a raffinate phase comprising solvent from the cannabinoid-contacting extract feed; and
    recovering the concentrated cannabinoid product from the extract phase.

2. The process as set forth in claim 1 wherein the concentration of cannabinoids in the first permeate is higher than the concentration of cannabinoids in the first retentate.

3. The process as set forth in claim 1,
    wherein at least about 75% by weight of compounds having a molecular weight greater than about 500 daltons contained in the pre-treated extract are retained in the first retentate.

4. The process as set forth in claim 1 wherein the first filter is selected from the group consisting of an organic solvent stable (OSS) filter, a membrane, or a ceramic filter.

5. The process as set forth in claim 4 wherein the first filter is a tangential flow membrane.

6. The process as set forth in claim 1 wherein the pre-treated extract is contacted with the first filter at a pressure not greater than about 50 bar.

7. The process as set forth in claim 1 wherein water is added to the pre-treated extract in an amount sufficient to reduce the concentration of solvent from the cannabinoid-containing extract feed to less than about 80 wt %.

8. The process as set forth in claim 1 wherein the adsorbent is selected from the group consisting of one or more of activated charcoal, silica, magnesium silicate, and diatomaceous earth.

9. The process as set forth in claim 8 wherein the weight ratio of activated charcoal to raw *cannabis* plant material used to prepare the cannabinoid-containing extract feed is at least about 1:2.

10. The process as set forth in claim 1 wherein the first permeate is combined with the extractant and a brine solution to form the filtrate extraction mixture.

11. The process as set forth in claim 1 wherein the recovery of the concentrated cannabinoid product comprises drying the extract phase with a drying agent.

12. The process as set forth in claim 11 wherein the drying agent is selected from the group consisting of metal salts, alumino silicates, and mixtures thereof.

13. The process as set forth in claim 1 wherein the cannabinoid-containing extract feed has a water content of less than about 25 wt %.

14. The process as set forth in claim 1 wherein the extractant is a medium-chain triglyceride (MCT) oil selected from the group consisting of one or more of palm kernel oil, coconut oil, olive oil, sesame seed oil, almond oil, grape seed oil, and hemp seed oil.

15. The process as set forth in claim 1 wherein the process is performed at a temperature lower than about 78° C.

16. The process as set forth in claim 1 wherein large molecule impurities are adsorbed from the cannabinoid-containing extract feed with an adsorbent at a temperature between about 5° C. and about 50° C.

17. The process as set forth in claim 1 wherein the cannabinoid-containing extract feed, pre-treated extract, and first permeate further comprises terpenes, flavonoids, or combinations thereof.

18. A process for preparing a concentrated cannabinoid product, comprising:
   contacting a cannabinoid-containing extract feed comprising cannabinoids and a solvent with a solid adsorbent to adsorb large molecule impurities from the cannabinoid-containing extract and produce a pre-treated extract;
   contacting the pre-treated extract with a first filter having a 400-5,000 dalton MWCO (molecular weight cut-off) to produce a first retentate comprising large molecular weight impurities and a first permeate comprising cannabinoids;
   contacting the first permeate with a second filter having a 150-1,000 dalton MWCO to produce a second retentate comprising cannabinoids and a second permeate comprising small molecular weight impurities, wherein the concentration of cannabinoids in second retentate is higher than the concentration of cannabinoids in the second permeate;
   combining the second retentate and a liquid phase extractant to form a filtrate extraction mixture comprising an extract phase comprising cannabinoids and a raffinate phase comprising solvent from the cannabinoid-containing extract feed; and
   recovering the concentrated cannabinoid product from the extract phase.

19. The process as set forth in claim 18 wherein the concentration of cannabinoids in the first permeate is higher than the concentration of cannabinoids in the first retentate.

20. The process as set forth in claim 18,
   wherein at least about 75% by weight of compounds having a molecular weight greater than about 500 daltons contained in the pre-treated extract are retained in the first retentate; and
   wherein at least about 75% by weight of compounds having a molecular weight less than about 200 daltons contained in the first permeate are transferred to the second permeate.

21. A process for preparing a concentrated cannabinoid product, comprising
   contacting a cannabinoid-containing extract feed comprising cannabinoids and a solvent with a solid adsorbent to adsorb large molecule impurities from the cannabinoid-containing extract feed and produce a pre-treated extract;
   contacting the pre-treated extract with a first filter having a 400-5,000 dalton MWCO (molecular weight cut-off) to produce a first retentate comprising large molecular weight impurities and a first permeate comprising cannabinoids;
   adding water to the first permeate to form a water-adjusted first permeate having a water content of from about 20 wt % to about 40 wt %;
   contacting the water-adjusted first permeate with the first filter to produce a second permeate comprising small molecular weight impurities and a second retentate comprising cannabinoids, wherein the concentration of cannabinoids in the second retentate is higher than the concentration of cannabinoids in the second permeate;
   combining the second retentate and a liquid phase extractant to form a filtrate extraction mixture comprising an extract phase comprising cannabinoids and a raffinate phase comprising solvent from the cannabinoid-containing extract feed; and
   recovering the concentrated cannabinoid product from the extract phase.

22. The process as set forth in claim 21 wherein the concentration of cannabinoids in the first permeate is higher than the concentration of cannabinoids in the first retentate.

23. The process as set forth in claim 21,
   wherein at least about 75% by weight of compounds having a molecular weight greater than about 500 daltons contained in the pre-treated extract are retained in the first retentate; and
   wherein at least about 75% by weight of compounds having a molecular weight less than about 200 daltons contained in the water-adjusted first permeate are transferred to the second permeate.

* * * * *